(12) United States Patent
Wu et al.

(10) Patent No.: US 8,398,966 B2
(45) Date of Patent: Mar. 19, 2013

(54) IL-1 BINDING PROTEINS

(75) Inventors: Chengbin Wu, Shanghai (CN); Chung-ming Hsieh, Newtown, MA (US); Renee Miller, N. Grosvenordale, CT (US); Dominic J. Ambrosi, Shrewsbury, MA (US)

(73) Assignee: AbbVie Inc., North Chicago, IL (US)

( * ) Notice: Subject to any disclaimer, the term of this patent is extended or adjusted under 35 U.S.C. 154(b) by 129 days.

(21) Appl. No.: 12/905,499

(22) Filed: Oct. 15, 2010

(65) Prior Publication Data

US 2011/0142761 A1 Jun. 16, 2011

Related U.S. Application Data

(60) Provisional application No. 61/251,856, filed on Oct. 15, 2009.

(51) Int. Cl.
*A61K 39/395* (2006.01)
*C07K 16/24* (2006.01)

(52) U.S. Cl. ............... 424/85.2; 530/387.3; 530/388.23; 530/389.2

(58) Field of Classification Search .................. None
See application file for complete search history.

(56) References Cited

U.S. PATENT DOCUMENTS

| | | | |
|---|---|---|---|
| 7,491,516 B2 | 2/2009 | Collinson et al. | |
| 7,612,181 B2 | 11/2009 | Wu et al. | |
| 8,258,268 B2 | 9/2012 | Wu et al. | |
| 2005/0042664 A1 | 2/2005 | Wu et al. | |
| 2007/0071675 A1 | 3/2007 | Wu et al. | |
| 2008/0118506 A1 | 5/2008 | Wu et al. | |
| 2009/0215992 A1 | 8/2009 | Wu et al. | |
| 2009/0232736 A1 | 9/2009 | Collinson et al. | |
| 2010/0047239 A1 | 2/2010 | Wu et al. | |
| 2010/0221179 A1 | 9/2010 | Wu et al. | |
| 2011/0016506 A1 | 1/2011 | Lu et al. | |
| 2011/0280800 A1 | 11/2011 | Wu et al. | |

FOREIGN PATENT DOCUMENTS

| | | |
|---|---|---|
| WO | WO 2008/055206 A1 | 8/2008 |
| WO | WO 2008/055206 A2 | 8/2008 |

OTHER PUBLICATIONS

International Search Report & Written Opinion from PCT/US2010/052849, dated Feb. 28, 2011.
International Preliminary Report on Patentability from PCT/US2010/052849, dated Nov. 16, 2011.

*Primary Examiner* — Prema Mertz
(74) *Attorney, Agent, or Firm* — Lathrop & Gage LLP; James H. Velema, Esq.

(57) ABSTRACT

The present invention describes IL-1β binding proteins, including chimeric, CDR-grafted, and humanized antibodies that bind IL-1β. Binding proteins of the invention have high affinity for IL-1β and neutralize IL-1β activity. A binding protein of the invention can be a full-length antibody or an IL-1β-binding portion thereof. Methods of making and methods of using the binding proteins of the invention are also described. The IL-1β binding proteins of the invention are useful for detecting IL-1β and for inhibiting IL-1β activity, including in a human subject suffering from a disease or disorder in which IL-1β activity is detrimental.

27 Claims, No Drawings

IL-1 BINDING PROTEINS

CROSS-REFERENCE TO RELATED APPLICATION

This application claims the benefit of priority to U.S. Provisional Application No. 61/251,856 filed Oct. 15, 2009, the entire contents of which is incorporated herein by reference for any purpose.

SEQUENCE LISTING

The instant application contains a Sequence Listing which has been submitted in ASCII format via EFS-Web and is hereby incorporated by reference in its entirety. Said ASCII copy, created on Nov. 22, 2010, is named 10201US0.txt and is 32,474 bytes in size.

FIELD OF THE INVENTION

The present invention relates to IL-1 binding proteins, and specifically to their uses in the prevention and/or treatment of IL-1 mediated diseases.

BACKGROUND OF THE INVENTION

Cytokines, such as interleukin-1 (IL-1) and tumor necrosis factor (TNF), are molecules produced by a variety of cells, such as monocytes and macrophages, which are mediators of inflammatory processes. Interleukin-1 is a cytokine with a wide range of biological and physiological effects, including fever, prostaglandin synthesis (m, e.g., fibroblasts, muscle cells and endothelial cells), T-lymphocyte activation, and interleukin-2 production.

The Interleukin-1 superfamily: The original members of the IL-1 superfamily are IL-1α, IL-1β, and the IL-1 Receptor antagonist (IL-1RA). IL-1α and -β are pro-inflammatory cytokines involved in immune defense against infection. The IL-1Rα is a molecule that competes for receptor binding with IL-1α and IL-1β, blocking their role in immune activation. Recent years have seen the addition of other molecules to the IL-1 superfamily including IL-18 (see Dinarello (1994) FASEB J. 8(15):1314-3225; Huising et al. (2004) Dev. Comp. Immunol. 28(5):395-413) and six more genes with structural homology to IL-1α, IL-1β or IL-1RA. These latter six members are named IL1F5, IL1F6, IL1F7, IL1F8, IL1F9, and IL1F10. In accordance, IL-1α, IL-1β, and IL-1RA have been renamed IL-1F1, IL-1F2, and IL-1F3, respectively (see Sims et al. (2001) Trends Immunol. 22(10):536-537; Dunn et al. (2001) Trends Immunol. 22(10):533-536). A further putative member of the IL-1 family has been described called IL-33 or IL-1F11, although this name is not officially accepted in the HGNC gene family nomenclature database.

Both IL-1α and IL-1β are produced by macrophages, monocytes and dendritic cells. They form an important part of the inflammatory response of the body against infection. These cytokines increase the expression of adhesion factors on endothelial cells to enable transmigration of leukocytes, the cells that fight pathogens, to sites of infection and re-set the hypothalamus thermoregulatory center, leading to an increased body temperature which expresses itself as fever. IL-1 is therefore calledan endogenous pyrogen. The increased body temperature helps the body's immune system to fight infection. IL-1 is also important in the regulation of hematopoiesis. IL-1α is a pleiotropic cytokine involved in various immune responses, inflammatory processes, and hematopoiesis. IL-1α is produced by activated macrophages, stimulates thymocyte proliferation by inducing IL-2 release, B-cell maturation and proliferation, and fibroblast growth factor activity. IL-1α proteins are involved in the inflammatory response, being identified as endogenous pyrogens, and are reported to stimulate the release of prostaglandin and collagenase from synovial cells. It is produced as a proprotein that is proteolytically processed by calpain and released in a mechanism that is still not well studied. This gene and eight other interleukin 1 family genes form a cytokine gene cluster on chromosome 2. IL-1α and its disease-causing effects are described in detail in Ibelgaufts, Lexikon Zytokine (Cytokine Dictionary), Medikon Verlag, Munich 1992, and in the literature cited therein. Reference is also made to the undesirable effects of IL-1α in, for example, Oppenheim et al. (1986) Immunol. Today 7:45-56, Durum et al. (1985) Ann. Rev. Immunol. 3:263-287 and Synnons et al. (1989) Lymphokine Res. 8:365-372. IL-1α was originally termed "catabolin" because of its effect in increasing cartilage resorption, but also as "monocyte cell factor" (MCF) because of its stimulatory effect on collagenase and prostaglandin in synovial cells, and as "leucocyte endogenous factor" (LEM) having a stimulatory effect on acute phase reactions. In addition, IL-1α has a broad spectrum of biological activities, since IL-1α is synthesized by many different cells, such as monocytes, macrophages, fibroblasts, endothelial cells and lymphocytes, and many cells possess specific receptors for IL-1α. IL-1α therefore occupies a central position as the trigger for various disorders and symptoms of disorders. These disorders are often predominantly serious disorders for which there is little or no treatment. It has been suggested that the polymorphism of these genes is associated with rheumatoid arthritis and Alzheimer's disease. IL-1 in general has been implicated in many human diseases, including arthritis, pulmonary fibrosis, diseases of the central nervous system, diabetes mellitus, and certain cardiovascular diseases.

IL-1β production in peripheral tissue has also been associated with hyperalgesia (increased sensitivity to pain) associated with fever (Morgan et al. (2004) Brain Res. 1022(1-2): 96-100). For the most part, these two forms of IL-1 bind to the same cellular receptor. This receptor is composed of two related, but non-identical, subunits that transmit intracellular signals via a pathway that is mostly shared with certain other receptors. These include the Toll family of innate immune receptors and the receptor for IL-18. IL-1α and IL-1β also possess similar biological properties, including induction of fever, slow wave sleep, and neutrophilia, T- and B-lymphocyte activation, fibroblast proliferation, cytotoxicity for certain cells, induction of collagenases, synthesis of hepatic acute phase proteins, and increased production of colony stimulating factors and collagen.

cDNAs encoding the two distinct forms of IL-1 have been isolated and expressed; these cDNAs represent two different gene products, termed IL-1β (Auron et al. (1984) *Proc. Natl. Acad. Sci. USA* 81:7909) and IL-1α (Lomedico et al. (1984) Nature 312:458). IL-1β is the predominant form produced by human monocytes both at the mRNA and protein levels. The two forms of human IL-1 share only 26% amino acid homology. Despite their distinct polypeptide sequences, the two forms of IL-1 have structural similarities (Auron et al. (1985) *J. Mol. Cell. Immunol.* 2:169), in that the amino acid homology is confined to discrete regions of the IL-1 molecule.

IL-1α and IL-1β are produced as precursor peptides. In other words they are made as a long protein that is then processed to release a shorter, active molecule, which is called the mature protein. Mature IL-1β, for example, is released from Pro-IL-1β following cleavage by a certain member of the caspase family of proteins, called caspase-1 or the interleukin-1 converting enzyme (ICE). The 3-dimensional structure of the mature forms of each member of the human IL-1 superfamily is composed of 12-14 β-strands producing a barrel-shaped protein.

There is a need in the art for improved antibodies that bind IL-1β for use in new therapies against IL-1β associated diseases and for use in detecting IL-1β in samples and tissues.

SUMMARY OF THE INVENTION

The present invention provides a novel family of binding proteins, including monoclonal antibodies (mAbs), CDR grafted antibodies, humanized antibodies, affinity matured antibodies, and fragments thereof, capable binding human IL-1β, binding with high affinity, and binding and neutralizing IL-1β. The invention provides a therapeutic means with which to inhibit human IL-1β and provides compositions and methods for treating diseases and disorders associated with increased levels of IL-1β particularly inflammatory disorders. The invention also provides an antibody, or antigen binding portion thereof, capable of binding IL-1β wherein said antibody, or antigen binding portion thereof, capable of binding IL-1β comprises an amino acid sequence selected from the group consisting of SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39 and SEQ ID NO: 40. In another embodiment, the invention provides means for detecting and/or measuring human IL-1β in samples, mixtures, and tissues.

In one aspect of the invention, the isolated binding protein is capable of binding human IL-1β and comprises at least one CDR comprising an amino acid sequence selected from the group consisting of residues 31-35 of SEQ ID NO:26 (CDR-H1); residues 50-65 of SEQ ID NO:26 (CDR-H2); residues 98-111 of SEQ ID NO:26 (CDR-H3); residues 24-34 of SEQ ID NO:27 (CDR-L1); residues 50-56 of SEQ ID NO:27 (CDR-L2); and residues 89-97 of SEQ ID NO:27 (CDR-L3).

In another embodiment, a binding protein comprises at least three CDRs that are selected from a variable domain CDR set, wherein the variable domain CDR set is selected from the group consisting of a VH CDR Set comprising residues 31-35 of SEQ ID NO:26 (CDR-H1); residues 50-65 of SEQ ID NO:26 (CDR-H2); and residues 98-111 of SEQ ID NO:26 (CDR-H3); and a VL CDR Set comprising residues 24-34 of SEQ ID NO:27 (CDR-L1); residues 50-56 of SEQ ID NO:27 (CDR-L2); and residues 89-97 of SEQ ID NO:27 (CDR-L3).

In an embodiment, a binding protein comprises a variable heavy chain (VH) set of three CDRs and also comprises a variable light chain (VL) set of three CDRS.

In another embodiment of the invention, an IL-1β binding protein comprising one or more CDRs described above further comprises a corresponding human heavy chain acceptor framework sequence (for CDR-H1, CDR-H2, and CDR-H3 sequences) and/or a corresponding human light chain acceptor framework sequence (for CDR-L1, CDR-L2, and CDR-L3 sequences). In an embodiment, a human heavy chain acceptor framework sequence of a binding protein of the invention is selected from any of the human heavy chain acceptor framework sequences of Table 3 and a human light chain acceptor framework sequence of binding protein of the invention is selected from any of the human light chain acceptor framework sequences of Table 4. Accordingly, in an embodiment, a human acceptor framework sequence of a binding protein according to the invention is selected from the group consisting of SEQ ID NOS: 10-17 (which are human heavy chain acceptor framework sequences) and SEQ ID NOS: 18-25 (which are human light chain acceptor framework sequences). In an embodiment, the human acceptor framework sequences are selected from the groups consisting of SEQ ID NOS: 10-13 (heavy chain), 14-17 (heavy chain), 18-21 (light chain), and 22-25 (light chain).

An IL-1β binding protein may comprise a human acceptor framework comprising at least one framework region (FR) amino acid substitution, wherein the amino acid sequence of the framework is at least 65% identical to the sequence of said human acceptor framework and comprises at least 70 amino acid residues identical to said human acceptor framework.

In another embodiment, an IL-1β binding protein of the invention comprises a human acceptor framework, wherein said acceptor framework comprises at least one framework region amino acid substitution at a key residue, said key residue selected from the group consisting of:
a residue adjacent to a CDR;
a glycosylation site residue;
a rare residue;
a residue capable of interacting with human IL-1β;
a residue capable of interacting with a CDR;
a canonical residue;
a contact residue between heavy chain variable region and light chain variable region;
a residue within a Vernier zone; and
a residue in a region that overlaps between a Chothia-defined variable heavy chain CDR1 and a Kabat-defined first heavy chain framework.

In an embodiment, an IL-1β binding protein may comprise a key residue, wherein said key residue is selected from the group consisting of: 1H, 12H, 24H, 27H, 29H, 37H, 48H, 49H, 67H, 71H, 73H, 76H, 78H, 94H, 1L, 2L, 3L, 4L, 43L, 49L, 64L, 83L (all Kabat numbering). In yet another embodiment, an IL-1β binding protein according to the invention comprises a consensus human variable domain that is a consensus human variable domain described herein. In another aspect, the invention provides IL-1β binding proteins comprising at least one variable domain comprising an amino acid sequence selected from the group consisting of: SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

In another aspect, the invention provides IL-1β binding proteins comprising a variable heavy chain polypeptide comprising an amino acid sequence selected from the group consisting of SEQ ID NO:28, SEQ ID NO:29, SEQ ID NO:30, SEQ ID NO:31, SEQ ID NO:32, and SEQ ID NO:33, wherein the binding proteins are capable of binding human IL-1β. In another aspect, the invention provides IL-1β binding proteins comprising a variable light chain polypeptide comprising an amino acid sequence selected from the group consisting of SEQ ID NO:34, SEQ ID NO:35, SEQ ID NO:36, SEQ ID NO:37, SEQ ID NO:38, SEQ ID NO:39, and SEQ ID NO:40, wherein the binding proteins are capable of binding human IL-1β.

In yet another aspect, the invention provides binding proteins comprising a variable heavy chain polypeptide comprising an amino acid sequence selected from the group consisting of SEQ ID NO:28, SEQ ID NO:29, SEQ ID NO:30, SEQ ID NO:31, SEQ ID NO:32, and SEQ ID NO:33, and a variable light chain polypeptide comprising an amino acid sequence selected from the group consisting of SEQ ID NO:34, SEQ ID NO:35, SEQ ID NO:36, SEQ ID NO:37, SEQ ID NO:38, SEQ ID NO:39, and SEQ ID NO:40, wherein the binding proteins are capable of binding human IL-1β.

In yet another aspect, the binding proteins comprise a variable heavy chain polypeptide and a variable light chain polypeptide selected from the group consisting of SEQ ID NO:30 and SEQ ID NO:36; SEQ ID NO:30 and SEQ ID NO:37; SEQ ID NO:30 and SEQ ID NO:39; and SEQ ID NO:30 and SEQ ID NO:40.

In yet another aspect, the binding proteins comprise a variable heavy chain polypeptide and a variable light chain polypeptide selected from the group consisting of SEQ ID NO:33 and SEQ ID NO:36; SEQ ID NO:33 and SEQ ID NO:37; SEQ ID NO:33 and SEQ ID NO:39; and SEQ ID NO:33 and SEQ ID NO:40.

In another aspect, the invention provide a binding protein described above, wherein said binding protein is an immunoglobulin molecule, a disulfide linked Fv, a monoclonal antibody, a scFv, a chimeric antibody, a single domain antibody, a CDR-grafted antibody, a diabody, a humanized antibody, a multispecific antibody, an Fab, a dual specific antibody, a DVD-Ig™ binding protein, a Fab', a bispecific antibody, an F(ab')2, or an Fv.

In another aspect, a binding protein described above comprises a heavy chain immunoglobulin constant domain selected from the group consisting of a human IgM constant domain, a human IgG4 constant domain, a human IgG1 constant domain, a human IgE constant domain, a human IgG2 constant domain, a human IgG3 constant domain, and a human IgA constant domain. In yet another aspect, a binding protein of the invention further comprises a heavy chain constant region having an amino acid sequence selected from the group consisting of SEQ ID NO:2 and SEQ ID NO:3, and additionally a light chain constant region having an amino acid sequence selected from the group consisting of SEQ ID NO:4 and SEQ ID NO:5. In another aspect of the invention, binding proteins of the invention are capable of modulating a biological function of human IL-1β and additionally capable of neutralizing human IL-1β. In one aspect of the invention, a binding protein of the invention has an on rate constant (Kon) to said target selected from the group consisting of at least about $10^2 M^{-1}s^{-1}$; at least about $10^3 M^{-1}$; at least about $10^4 M^{-1}s^{-1}$; at least about $10^5 M^{-1}s^{-1}$; and at least about $10^6 M^{-1}s^{-1}$, as measured by surface plasmon resonance.

In another aspect, an IL-1β binding protein of the invention has an off rate constant (Koff) to the target selected from the group consisting of at most about $10^{-3}s^{-1}$; at most about $10^{-4}s^{-1}$; at most about $10^{-5}s^{-1}$; and at most about $10^{-6}s^{-1}$, as measured by surface plasmon resonance.

In yet another aspect, an IL-1β binding protein of the invention has a dissociation constant (KD) to the IL-1β target molecule selected from the group consisting of at most about $10^{-7}M$; at most about $10^{-8}M$; at most about $10^{-9}M$; at most about $10^{-10}M$; at most about $10^{-11}M$; at most about $10^{-12}M$; and at most about $10^{-13}M$. Additionally, the binding proteins have a dissociation constant (KD) to IL-1β selected from the group consisting of about $1.31 \times 10^{-10}M$; about $1.47 \times 10^{10}M$; about $1.61 \times 10^{-10}M$; about $1.86 \times 10^{-10}M$; about $2.02 \times 10^{-10}M$; about $2.06 \times 10^{10}M$; about $2.3 \times 10^{-10}M$; and about $2.84 \times 10^{-10}M$.

In another aspect of the invention, binding proteins of the invention further comprise an agent selected from the group consisting of an immunoadhesion molecule, an imaging agent, a therapeutic agent, and a cytotoxic agent. The imaging agent can be any imaging agent known in the art, including but not limited to, a radiolabel (including, but not limited to, 3H, 14C, 35S, 90Y, 99Tc, 111In, 125I, 131I, 177Lu, 166Ho, and 153Sm), an enzyme, a fluorescent label, a luminescent label, a bioluminescent label, a magnetic label, or a biotin molecule. The therapeutic or cytotoxic agent can be an antimetabolite, an alkylating agent, an antibiotic, a growth factor, a cytokine, an anti-angiogenic agent, an anti-mitotic agent, an anthracycline, a toxin, and an apoptotic agent.

In another aspect, an IL-1β binding protein of the invention is glycosylated. In an embodiment, the glycosylation is a human glycosylation pattern.

In one aspect of the invention, an IL-1β binding protein is a crystal. In one embodiment, the crystal is a carrier-free pharmaceutical controlled release crystal. In another embodiment, the crystallized binding protein has a greater half life in vivo than its soluble counterpart. In still another embodiment, the crystallized binding protein retains biological activity after crystallization.

One aspect of the invention pertains to an isolated nucleic acid encoding any one of the binding proteins, or antigen-binding portion thereof, disclosed above. In an embodiment, the invention provides an isolated nucleic acid that encodes a polypeptide selected from the group consisting of: a polypeptide comprising a heavy chain variable domain (VH), wherein the heavy chain variable domain comprises a CDR-H1, a CDR-H2, and/or a CDR-H3 described herein; a polypeptide comprising a light chain variable domain (VL), wherein the light chain variable domain comprises a CDR-L1, a CDR-L2, and/or a CDR-L3 described herein, or a combination of both polypeptides.

A further embodiment of the invention provides a vector comprising the isolated nucleic acid disclosed above wherein the vector is selected from the group consisting of pcDNA, pTT (Durocher et al. (2002) Nucl. Acids Res. 30(2e9):1-9), pTT3 (pTT with additional multiple cloning site), pEFBOS (Mizushima and Nagata (1990) Nucl. Acids Res. 18(17): 5322), pBV, pJV, pBJ, and pHybE.

In another aspect, a host cell is transformed with a vector disclosed herein. In one embodiment, the host cell is a prokaryotic cell including, but not limited to, *Escherichia coli*. In another embodiment, the host cell is a eukaryotic cell including, but not limited to, a protist cell, an animal cell, a plant cell, and a fungal cell. In another embodiment, the host cell is a mammalian cell including, but not limited to, CHO cells and COS cells, or a fungal cell such as, for example, *Saccharomyces cerevisiae*, or an insect cell such as, for example, Sf9.

In another aspect, the invention provides a method of producing a binding protein that binds IL-1β, comprising culturing any one of the host cells disclosed above in a culture medium under conditions sufficient to produce a binding protein that binds IL-1β. In another embodiment, the invention provides a binding protein produced according to the method disclosed herein. In an embodiment, the invention provides a composition for the release of a binding protein wherein the composition comprises a formulation which in turn comprises a crystallized binding protein, crystallized antibody construct, or crystallized antibody conjugate as disclosed herein, an ingredient, and at least one polymeric carrier. In an embodiment, the polymeric carrier is one or more polymers selected from the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutyrate), poly (caprolactone), poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. In another aspect, the ingredient is selected from the group consisting of albumin, sucrose, trehalose, lactitol, gelatin, hydroxypropyl-b-cyclodextrin, methoxypolyethylene glycol and polyethylene glycol. In another embodiment, the invention provides a method for treating a mammal comprising the step of administering to the mammal an effective amount of a composition disclosed herein.

The invention also provides pharmaceutical compositions comprising an IL-1β binding protein (or an IL-1β binding portion thereof) as disclosed herein and a pharmaceutically acceptable carrier. Such a pharmaceutical composition of the invention can further comprise at least one additional agent. In a particular embodiment, a pharmaceutical composition of the invention comprises at least one additional agent for treating a disorder in which IL-1β activity is detrimental. In another embodiment, an additional agent is selected from the group consisting of a therapeutic agent, an imaging agent, a cytotoxic agent, an angiogenesis inhibitor, a kinase inhibitor, a co-stimulation molecule blocker, an adhesion molecule blocker, an anti-cytokine antibody, a functional fragment of an anti-cytokine antibody, methotrexate, cyclosporin, rapamycin, FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive agent, a growth hormone, a hormone replacement drug, a radiopharmaceutical, an antidepressant, an antipsychotic, a stimulant, an asthma medication, a beta agonist, an inhaled steroid, an oral steroid, an epinephrine or analog thereof, a cytokine, and a cytokine antagonist.

In another aspect, the invention provides a method for inhibiting human IL-1β activity comprising contacting human IL-1β with a binding protein disclosed herein such that human IL-1β activity is inhibited. In another aspect, the invention provides a method for inhibiting human IL-1β activity in a human subject suffering from a disorder in which IL-1β activity is detrimental, comprising administering to the human subject a binding protein disclosed herein such that human IL-1β activity in the human subject is inhibited and treatment is achieved.

In another aspect, the invention provides a method of treating (e.g., curing, suppressing, ameliorating, inhibiting, delaying, or preventing the onset of, or preventing recurrence or relapse of) an IL-1β associated disorder in a subject. In an embodiment, the method includes administering to the subject an IL-1β binding protein, e.g., an IL-1β antagonist, such as an anti-IL-1β antibody, or fragment thereof, as described herein, in an amount sufficient to treat or prevent the IL-1β associated disorder. The IL-1β antagonist can be administered to the subject, alone or in combination with other therapeutic modalities as described herein. In an aspect of the invention, an IL-1β binding protein, or binding portion thereof, can be employed to detect human IL-1β using any of a variety of antibody-based immunodetection systems available in the art that employ an antibody to detect a desired target antigen (or epitope thereof). Such immunodetection systems include, but are not limited to, immunoprecipitation, immunblotting (Western blot, immunodot blot), enzyme-linked immunsorbent assay (ELISA), radioimmunoassay (RIA), tissue immunohistochemistry, surface plasmon resonance (SPR), sandwich immunoassay, affinity methods (e.g., affinity beads, affinity columns), immunocompetition assay, immunochip assay (employing binding protein attached to a silicon chip), and fluorescence activated cell sorting (FACS).

For some immunodetection systems, an IL-1β binding protein (or binding portion thereof) as described herein is attached to a solid substrate using methods available in the art for attaching antibody molecules to the same solid substrate so that the attached binding protein retains its ability to bind human IL-1β during use in the particular immunodetection system. Such solid substrates include, but are not limited to, a cellulose-based filter paper (e.g., cellulose, nitrocellulose, cellulose acetate filters), a nylon filter or membrane, a plastic surface (e.g., of a microtiter plate or dip stick), a glass substrate (e.g., beads, slides, glass wool), a polymeric particle (e.g., agarose, polyacrylamide), and a silicon chip. In another aspect, the invention provides a method for detecting the presence of IL-1β in a sample in vitro (e.g., a biological sample, such as whole blood, serum, plasma, urine, saliva, tissue biopsy). The method can be used to diagnose a disease or disorder, e.g., an immune cell-associated disorder. The method includes: (i) contacting a test sample or a control sample with an IL-1a binding protein (or binding portion thereof) as described herein; and (ii) detecting formation of a complex between the binding protein, or binding portion thereof, and the test sample or the control sample, wherein a statistically significant change in the formation of the complex in the test sample relative to the control sample, or relative to formation of the complex in another test sample taken at an earlier time point, is indicative of the presence of IL-1β in the sample.

In yet another aspect, the invention provides a method for detecting the presence of IL-1β in vivo (e.g., in vivo imaging in a subject). The method is used to diagnose a disease or disorder, e.g., an IL-1β-associated disorder. The method includes: (i) administering an IL-1β binding protein, or binding portion thereof, as described herein to a test subject or a control subject under conditions that allow binding of the binding protein, or binding portion thereof, to IL-1β; and (ii) detecting formation of a complex between the binding protein, or binding portion thereof, and IL-1β, wherein a statistically significant change in the formation of the complex in the test subject relative to the control subject, or relative to the formation of the complex in the test subject at an earlier time point, is indicative of the presence of IL-1β.

In another aspect, the binding proteins of the invention are useful for treating a disorder selected from the group consisting of rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpura, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic polyglandular deficiency type I and polyglandular deficiency type II, Schmidt's syndrome, adult (acute) respiratory distress syndrome, alopecia, alopecia areata, seronegative arthropathy, arthropathy, Reiter's disease, psoriatic arthropathy, ulcerative colitic arthropathy, enteropathic synovitis, chlamydia, *yersinia* and *salmonella* associated arthropathy, spondyloarthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, hepatitis B, hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, drug-induced hepatitis, non-alcoholic steatohepatitis, allergy and asthma, group B streptococci (GB S) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), abetalipoproteinemia, acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti CD3 therapy, antiphospholipid syndrome, anti-receptor hypersensitivity reactions, aortic and peripheral aneurysms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, dementia pugilistica, demyelinating diseases, dengue hemorrhagic fever, dermatitis, dermatologic conditions, diabetes, diabetes mellitus, diabetic arteriosclerotic disease, diffuse Lewy body disease, dilated congestive cardiomyopathy, disorders of the basal ganglia, Down's syndrome in middle age, drug-induced movement disorders induced by drugs which block CNS dopamine receptors, drug sensitivity, eczema, encephalomyelitis, endocarditis, endocrinopathy, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, Hashimoto's thyroiditis, hay fever, heart transplant rejection, hemachromatosis, hemodialysis, hemolytic uremic syndrome/thrombolytic thrombocytopenic purpura, hemorrhage, hepatitis A, His bundle arrhythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, asthenia, infantile spinal muscular atrophy, inflammation of the aorta, influenza A, ionizing radiation exposure, iridocyclitis/uveitis/optic neuritis, ischemia-reperfusion injury, ischemic stroke, juvenile rheumatoid arthritis (JRA), juvenile spinal muscular atrophy, Kaposi's sarcoma, kidney transplant rejection, *legionella*, leishmaniasis, leprosy, lesions of the corticospinal system, lipedema, liver transplant rejection, lymphedema, malaria, malignant lymphoma, malignant histiocytosis, malignant melanoma, meningitis, meningococcemia, metabolic/idiopathic, migraine headache, mitochondrial multi-system disorder, mixed connective tissue disease, monoclonal gammopathy, multiple myeloma, multiple systems degenerations (Mencel Dejerine-Thomas Shi-Drager and Machado-Joseph), myasthenia gravis, *mycrobacterium avium intracellulare, mycobacterium tuberculosis*, myelodysplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non- Hodgkin's lymphoma, occlusion of the abdominal aorta and its branches, occlusive arterial disorders, OKT3® therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherosclerotic disease, peripheral vascular disorders, peritonitis, pernicious anemia, *pneumocystis carinii pneumonia, pneumonia*, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, progressive supranucleo palsy, primary pulmonary hypertension, radiation therapy, Raynaud's phenomenon, Raynaud's disease, Refsum's disease, regular narrow QRS tachycardia, renovascular hypertension, reperfusion injury, restrictive cardiomyopathy, sarcomas, scleroderma, senile chorea, senile dementia of Lewy body type, seronegative arthropathies, shock, sickle cell anemia, skin allograft rejection, skin changes syndrome, small bowel transplant rejection, solid tumors, specific arrhythmias, spinal ataxia, spinocerebellar degenerations, streptococcal myositis, structural lesions of the cerebellum, subacute sclerosing panencephalitis, syncope, syphilis of the cardiovascular system, systemic anaphylaxis, systemic inflammatory response syndrome, systemic onset juvenile rheumatoid arthritis, T-cell or FAB ALL, telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, viral encephalitis/aseptic meningitis, viral-associated hemaphagocytic syndrome, Wernicke-Korsakoff syndrome, Wilson's disease, xenograft rejection of any organ or tissue, acute coronary syndromes, acute idiopathic polyneuritis, acute inflammatory demyelinating polyradiculoneuropathy, acute ischemia, adult Still's disease, alopecia areata, anaphylaxis, anti-phospholipid antibody syndrome, aplastic anemia, arteriosclerosis, atopic eczema, atopic dermatitis, autoimmune dermatitis, autoimmune disorder associated with *streptococcus* infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophic antiphospholipid syndrome, celiac disease, cervical spondylosis, chronic ischemia, cicatricial pemphigoid, clinically isolated syndrome (CIS) with risk for multiple sclerosis, conjunctivitis, childhood onset psychiatric disorder, chronic obstructive pulmonary disease (COPD), dacryocystitis, dermatomyositis, diabetic retinopathy, diabetes mellitus, disk herniation, disk prolapse, drug induced immune hemolytic anemia, endocarditis, endometriosis, endophthalmitis, episcleritis, erythema multiforme, erythema multiforme major, gestational pemphigoid, Guillain-Barré syndrome (GBS), hay fever, Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojunctivitis sicca, Kussmaul disease or Kussmaul-Meier disease, Landry's paralysis, Langerhan's cell histiocytosis, livedo reticularis, macular degeneration, microscopic polyangiitis, morbus bechterev, motor neuron disorders, mucous membrane pemphigoid, multiple organ failure, myasthenia gravis, myelodysplastic syndrome, myocarditis, nerve root disorders, neuropathy, non-A non-B hepatitis, optic neuritis, osteolysis, pauciarticular JRA, peripheral artery occlusive disease (PAOD), peripheral vascular disease (PVD), peripheral artery disease (PAD), phlebitis, polyarteritis nodosa (or periarteritis nodosa), polychondritis, polymyalgia rheumatica, poliosis, polyarticular JRA, polyendocrine deficiency syndrome, polymyositis, polymyalgia rheumatica (PMR), post-pump syndrome, primary Parkinsonism, prostatitis, pure red cell aplasia, primary adrenal insufficiency, recurrent neuromyelitis optica, restenosis, rheumatic heart disease, SAPHO (synovitis, acne, pustulosis, hyperostosis, and osteitis), scleroderma, secondary amyloidosis, shock lung, scleritis, sciatica, secondary adrenal insufficiency, silicone associated connective tissue disease, Sneddon-Wilkinson dermatosis, spondylitis ankylosans, Stevens-Johnson syndrome (SJS), systemic inflammatory response syndrome, temporal arteritis, toxoplasmic retinitis, toxic epidermal necrolysis, transverse myelitis, TRAPS (Tumor-necrosis factor receptor type 1 (TNFR)-Associated Periodic Syndrome); type B insulin resistance with acanthosis nigricans; type 1 allergic reaction, type II diabetes, urticaria, usual interstitial pneumonia (UIP), vasculitis, vernal conjunctivitis, viral retinitis, Vogt-Koyanagi-Harada syndrome (VKH syndrome), wet macular degeneration, and wound healing.

In one aspect, the binding proteins of the invention are used to treat rheumatoid arthritis, osteoarthritis, Crohn's disease, multiple sclerosis, insulin dependent diabetes mellitus and psoriasis. In another aspect, the binding proteins of the invention are also used to treat humans suffering from autoimmune diseases, in particular those associated with inflammation, including, ankylosing spondylitis, allergy, autoimmune diabetes, autoimmune uveitis.

In another aspect the invention provides a method of treating a patient suffering from a disorder in which human IL-1β is detrimental comprising the step of administering any one of the binding proteins described herein before, concurrent with, or after the administration of a second agent, as discussed above. In a another embodiment the additional therapeutic agent that can be coadministered and/or coformulated with one or more IL-1β antagonists, (e.g., anti-IL-1β antibodies or fragments thereof) includes, but is not limited to, TNF antagonists; a soluble fragment of a TNF receptor; ENBREL® (etanercept); TNF enzyme antagonists; TNF converting enzyme (TACE) inhibitors; muscarinic receptor antagonists; TGF-beta antagonists; interferon gamma; perfenidone; chemotherapeutic agents, methotrexate; leflunomide; sirolimus (rapamycin) or an analog thereof, CCI-779; COX2 or cPLA2 inhibitors; NSAIDs; immunomodulators; p38 inhibitors; TPL-2, MK-2 and NFkB inhibitors; budenoside; epidermal growth factor; corticosteroids; cyclosporine; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β antibodies; anti-IL-6 antibodies; growth factors; elastase inhibitors; pyridinyl-imidazole compounds; antibodies or agonists of TNF, LT, IL-1α, IL-1β, IL-2, IL-3, IL-4, IL-5, IL-6, IL-7, IL-8, IL-9, IL-10, IL-11, IL-12, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, EMAP-II, GM-CSF, FGF, or PDGF; antibodies of CD2, CD3, CD4, CD8, CD25, CD28, CD30, CD40, CD45, CD69, CD90 or their ligands; FK506; rapamycin; mycophenolate mofetil; ibuprofen; prednisolone; phosphodiesterase inhibitors; adensosine agonists; anti-thrombotic agents; complement inhibitors; adrenergic agents; IRAK, NIK, IKK, p38, or MAP kinase inhibitors; IL-1β converting enzyme inhibitors; TNFα converting enzyme inhibitors; T-cell signaling inhibitors; metalloproteinase inhibitors; 6-mercaptopurines; angiotensin converting enzyme inhibitors; soluble cytokine receptors; soluble p55 TNF receptor; soluble p75 TNF receptor; sIL-1RI; sIL-1RII; sIL-6R; anti-inflammatory cytokines; IL-4; IL-10; IL-11; and TGFβ.

In one embodiment, the pharmaceutical compositions disclosed herein are administered to a subject by at least one mode selected from the group consisting of parenteral, subcutaneous, intramuscular, intravenous, intra-articular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal routes.

One aspect of the invention provides at least one IL-1β anti-idiotypic antibody to at least one IL-1β binding protein of the invention. The anti-idiotypic antibody includes any protein or peptide containing molecule that comprises at least a portion of an immunoglobulin molecule such as, but not limited to, at least one complementarily determining region (CDR) of a heavy or light chain, or a ligand binding portion thereof, a heavy chain or light chain variable region, a heavy chain or light chain constant region, a framework region, or any portion thereof, that can be incorporated into a binding protein of the present invention.

DETAILED DESCRIPTION OF THE INVENTION

This invention pertains to IL-1β binding proteins, particularly anti-IL-1β antibodies, or antigen-binding portions thereof, that bind human IL-1β. Various aspects of the invention relate to antibodies and antibody fragments, and pharmaceutical compositions thereof, as well as nucleic acids, recombinant expression vectors and host cells for making such antibodies and IL-1β binding portions thereof. Methods of using the binding proteins of the invention to detect human IL-1β, to inhibit human IL-1β activity, either in vitro or in vivo; and to regulate gene expression are also encompassed by the invention.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the term "or" includes "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics, protein and nucleic acid chemistry and nucleic acid hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "polypeptide" means any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" means a protein or polypeptide that by virtue of its origin or source of derivation is not associated with naturally associated components that accompany it in its native state, is substantially free of other proteins from the same species, is expressed by a cell from a different species, or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" means the process of rendering a chemical species such as a polypeptide substantially free of naturally associated components by isolation, e.g., using protein purification techniques well known in the art.

The term "human IL-1β" (abbreviated herein as hIL-1β, or IL-1β) includes a pleiotropic cytokine involved in various immune responses, inflammatory processes, and hematopoiesis. The term human IL-1β includes recombinant human IL-1β (rh IL-1β) that can be prepared by standard recombinant expression methods.

TABLE 1

Sequence of Human IL-1β

| Protein | Sequence Identifier | Amino Acid Sequence<br>12345678901234567890123456789 0 |
|---|---|---|
| Human IL 1β | SEQ ID NO.: 1 | APVRSLNCTLRDSQQKSLVMSGPYELKALH<br>LQGQDMEQQVVFSMSFVQGEESNDKIPVAL<br>GLKEKNLYLSCVLKDDKPTLQLESVDPKNY<br>PKKKMEKRFVFNKIEINNKLEFESAQFPNW<br>YISTSQAENMPVFLGGTKGGQDITDFTMQF<br>VSS |

"Biological activity" refers to all inherent biological properties of IL-1β. Biological properties of IL-1β include but are not limited to binding IL-1 receptor; (other examples include: induction of fever, slow wave sleep, and neutrophilia, T- and B-lymphocyte activation, fibroblast proliferation, cytotoxicity for certain cells, induction of collagenases, synthesis of hepatic acute phase proteins, and increased production of colony stimulating factors and collagen).

The terms "specific binding" or "specifically binding" in reference to the interaction of an antibody, a protein, or a peptide with a second chemical species, mean that the interaction is dependent upon the presence of a particular structure (e.g., an antigenic determinant or epitope) on the chemical species, for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody" broadly refers to any immunoglobulin (Ig) molecule comprised of four polypeptide chains, two heavy (H) chains and two light (L) chains, or any functional fragment, mutant, variant, or derivative thereof, that retains the essential epitope binding features of an Ig molecule. Such mutant, variant, or derivative antibody formats are known in the art, nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen-binding portion" of an antibody refers to one or more fragments of an antibody that retain the ability to specifically bind to an antigen (e.g., hIL-1α). Thehe antigen-binding function of an antibody can be performed by fragments of a full-length antibody. Such antibody embodiments may also have bispecific, dual specific, or multi-specific formats; specifically binding to two or more different antigens. Examples of binding fragments encompassed within the term "antigen-binding portion" of an antibody include (i) an Fab fragment, which is a monovalent fragment consisting of the VL, VH, CL and CH1 domains; (ii) an F(ab')2 fragment, which is a bivalent fragment comprising two Fab fragments linked by a disulfide bridge at the hinge region; (iii) a Fd fragment consisting of the VH and CH1 domains; (iv) an Fv fragment consisting of the VL and VH domains of a single arm of an antibody, (v) a dAb fragment (Ward et al., (1989) *Nature* 341:544-546, PCT Publication No. WO 90/05144, which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies (scFvs) are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, et al. (1993) *Proc. Natl. Acad. Sci. USA* 90:6444-6448; Poljak, et al. (1994) *Structure* 2:1121-1123). Such antibody binding portions are known in the art (Kontermann and Dübel eds., *Antibody Engineering* (2001) Springer-Verlag. New York. 790 pp. (ISBN 3-540-41354-5)).

The term "antibody construct" refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger et al. (1993) *Proc. Natl. Acad. Sci. USA* 90:6444-6448; Poljak et al. (1994) *Structure* 2:1121-1123). An immunoglobulin constant domain refers to a heavy or light chain constant domain. Human IgG heavy chain (gamma) and light chain (kappa and delta) constant domain amino acid sequences are known in the art and represented in Table 2.

TABLE 2

Sequences Of Human 12G Heavy And Light Chain Constant Domains

| Protein | Sequence Identifier | Sequence<br>12345678901234567890123456789 0 |
|---|---|---|
| Ig gamma-1 constant region | SEQ ID NO.: 2 | ASTKGPSVFFLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTKTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVDWESNGQP<br>ENNYKTTPPVLDSDGSFFLYSKLTVDKSRW<br>QQGNVFSCSVMHEALHNHYTQKSLSLSPGK |
| Ig gamma-1 constant region mutant | SEQ ID NO.: 3 | ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPEAAGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK |
| Ig Kappa constant region | SEQ ID NO.: 4 | TVAAPSVFIFPPSDEQLKSGTASVVCLLNN<br>FYPREAKVQWKVDNALQSGNSQESVTEQDS<br>KDSTYSLSSTLTLSKADYEKHKVYACEVTH<br>QGLSSPVTKSFNRGEC |
| Ig Lambda constant region | SEQ ID NO.: 5 | QPKAAPSVTLFPPSSEELQANKATLVCLIS<br>DFYPGAVTVAWKADSSPVKAGVETTTPSKQ<br>SNNKYAASSYLSLTPEQWKSHRSYSCQVTH<br>EGSTVEKTVAPTECS |

Still further, an antibody or antigen-binding portion thereof may be part of a larger immunoadhesion molecule, formed by covalent or noncovalent association of the antibody or antigen binding portion thereof with one or more other proteins or peptides. Examples of such immunoadhesion molecules include use of the streptavidin core region to make a tetrameric scFv molecule (Kipriyanov et al. (1995) Human Antibod. and Hybridomas 6:93-101) and use of a cysteine residue, a marker peptide and a C-terminal polyhistidine tag to make bivalent and biotinylated scFv molecules (Kipriyanov et al. (1994) Mol. Immunol. 31:1047-1058). Antigen binding portions of antibodies, such as Fab and F(ab')$_2$ fragments, can be prepared from whole antibodies using conventional techniques, such as papain or pepsin digestion, respectively, of whole antibodies. Moreover, antibodies, antigen binding portions thereof, and immunoadhesion molecules can be obtained using standard recombinant DNA techniques, as described herein.

An "isolated antibody" refers to an antibody that is substantially free of other antibodies having different antigenic specificities (e.g., an isolated antibody that specifically binds hIL-1β is substantially free of antibodies that specifically bind antigens other than hIL-1β). An isolated antibody that specifically binds hIL-1β may, however, have cross-reactivity to other antigens, such as IL-1β molecules from other species. Moreover, an isolated antibody may be substantially free of other cellular material and/or chemicals.

The term "human antibody" is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" does not include antibodies in which CDR sequences derived from the germline of another mammalian species, such as a mouse, have been grafted onto human framework sequences.

The term "recombinant human antibody" includes all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom (1997) Trends Biotechnol. 15:62-70; Azzazy and Highsmith (2002) Clin. Biochem. 35:425-445; Gavilondo and Larrick (2000) BioTechniques 29:128-145; Hoogenboom and Chames (2000) Immunology Today 21:371-378), antibodies isolated from an animal (e.g., a mouse) that is transgenic for human immunoglobulin genes (see, e.g., Taylor et al. (1992) Nucl. Acids Res. 20:6287-6295; Kellermann and Green (2002) Curr. Opin. Biotechnol. 13:593-597; Little et al. (2000) Immunol. Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies that comprise heavy and light chain variable region sequences from one species and constant region sequences from another species, such as antibodies having murine heavy and light chain variable regions linked to human constant regions.

The term "CDR-grafted antibody" refers to antibodies that comprise heavy and light chain variable region sequences from one species but in which the sequences of one or more of the CDR regions of VH and/or VL regions are replaced with CDR sequences of another species, such as antibodies that have human heavy and light chain variable regions in which one or more of the human CDRs (e.g., CDR3) has been replaced with murine CDR sequences, for example, as obtained from a murine monoclonal antibody to human IL-1β.

The term "CDR" refers to the complementarity determining region within antibody variable sequences. There are three CDRs in each of the variable regions of the heavy chain and the light chain, which are designated CDR1, CDR2, and CDR3, for each of the variable regions. The term "CDR set" refers to a group of three CDRs that occur in a single variable region (i.e., VH or VL) of an antigen binding site. The exact boundaries of these CDRs have been defined differently according to different systems. The system described by Kabat (Kabat et al. (1987, 1991) Sequences of Proteins of Immunological Interest (National Institutes of Health, Bethesda, Md.) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk (1987) J. Mol. Biol. 196:901-917 and Chothia et al. (1989) Nature 342:877-883) found that certain sub-portions within Kabat CDRs adopt nearly identical peptide backbone conformations, despite having great diversity at the level of amino acid sequence. These sub-portions were designated as L1, L2, and L3 or H1, H2, and H3, where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan et al. (1995) FASEB J. 9:133-139 and MacCallum (1996) J. Mol. Biol. 262(5):732-745). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs.

The terms "Kabat numbering", "Kabat definition and "Kabat labeling" are used interchangeably herein. These terms refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad. Sci. 190:382-391 and Kabat et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The growth and analysis of extensive public databases of amino acid sequences of variable heavy and light regions over the past twenty years have led to the understanding of the typical boundaries between framework regions (FR) and CDR sequences within variable region sequences and enabled persons skilled in this art to accurately determine the CDRs according to Kabat numbering, Chothia numbering, or other systems. See, e.g., Martin, In Kontermann and Dübel, eds., Antibody Engineering (Springer-Verlag, Berlin, 2001), chapter 31, pages 432-433. A useful method of determining the amino acid sequences of Kabat CDRs within the amino acid sequences of variable heavy (VH) and variable light (VL) regions is provided below:

To identify a CDR-L1 amino acid sequence:

Starts approximately 24 amino acid residues from the amino terminus of the VL region;

Residue before the CDR-L1 sequence is always cysteine (C);

Residue after the CDR-L1 sequence is always a tryptophan (W) residue, typically Trp-Tyr-Gln (W-Y-Q), but also Trp-Leu-Gln (W-L-Q), Trp-Phe-Gln (W-F-Q), and Trp-Tyr-Leu (W-Y-L);

Length is typically 10 to 17 amino acid residues.

To identify a CDR-L2 amino acid sequence:

Starts always 16 residues after the end of CDR-L1;

Residues before the CDR-L2 sequence are generally Ile-Tyr (1-Y), but also Val-Tyr (V-Y), Ile-Lys (I-K), and Ile-Phe (I-F);

Length is always 7 amino acid residues.

To identify a CDR-L3 amino acid sequence:

Starts always 33 amino acids after the end of CDR-L2;

Residue before the CDR-L3 amino acid sequence is always a cysteine (C);

Residues after the CDR-L3 sequence are always Phe-Gly-X-Gly (F-G-X-G) (SEQ ID NO:6), where X is any amino acid;

Length is typically 7 to 11 amino acid residues.

To identify a CDR-H1 amino acid sequence:

Starts approximately 31 amino acid residues from amino terminus of VH region and always 9 residues after a cysteine (C);

Residues before the CDR-H1 sequence are always Cys-X-X-X-X-X-X-X (SEQ ID NO:7), where X is any amino acid;

Residue after CDR-H1 sequence is always a Trp (W), typically Trp-Val (W-V), but also Trp-Ile (W-I), and Trp-Ala (W-A);

Length is typically 5 to 7 amino acid residues.

To identify a CDR-H2 amino acid sequence:

Starts always 15 amino acid residues after the end of CDR-H1;

Residues before CDR-H2 sequence are typically Leu-Glu-Trp-Ile-Gly (L-E-W-I-G) (SEQ ID NO:8), but other variations also;

Residues after CDR-H2 sequence are Lys/Arg-Leu/Ile/Val/Phe/Thr/Ala-Thr/Ser/Ile/Ala (K/R-L/I/V/F/T/A-T/S/I/A);

Length is typically 16 to 19 amino acid residues.

To identify a CDR-H3 amino acid sequence:

Starts always 33 amino acid residues after the end of CDR-H2 and always 3 after a cysteine (C)'

Residues before the CDR-H3 sequence are always Cys-X-X (C-X-X), where X is any amino acid, typically Cys-Ala-Arg (C-A-R);

Residues after the CDR-H3 sequene are always Trp-Gly-X-Gly (W-G-X-G) (SEQ ID NO:9), where X is any amino acid;

Length is typically 3 to 25 amino acid residues.

The terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, at least 85%, at least 90%, at least 95%, at least 98%, or 100% of the amino acid sequences of one or more of the framework regions. In accordance with this embodiment, an acceptor may contain at least 1, at least 2, at least 3, at least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

The term "canonical" residue refers to a residue in a CDR or framework that defines a particular canonical CDR structure as defined by Chothia et al. (1987) J. Mol. Biol. 196:901-917; Chothia et al. (1992) J. Mol. Biol. 227:799. According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

The terms "donor" and "donor antibody" refer to an antibody providing one or more CDRs. In an embodiment, the donor antibody is an antibody from a species different from the antibody from which the framework regions are obtained or derived. In the context of a humanized antibody, the term "donor antibody" refers to a non-human antibody providing one or more CDRs.

The term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. A FR represents one of the four sub-regions, and FRs represents two or more of the four sub-regions constituting a framework region.

Human heavy chain and light chain acceptor sequences are known in the art. In one embodiment of the invention the human heavy chain and light chain acceptor sequences are selected from the sequences described in Table 3 and Table 4.

TABLE 3

Heavy Chain Acceptor Sequences

| SEQ ID No. | Protein region | Sequence 123456789012345678901234567890123456789012 |
|---|---|---|
| 10 | VH4-59 FR1 | QVQLQESGPGLVKPSETLSLTCTVSGGSIS |
| 11 | VH4-59 FR2 | WIRQPPGKGLEWIG |
| 12 | VH4-59 FR3 | RVTISVDTSKNQFSLKLSSVTAADT AVYYCAR |
| 13 | JH4 FR4 | WGQGTLVTVSS |
| 14 | VH3-53 FR1 | EVQLVESGGGLIQPGGSLRLSCAASGFTVS |
| 15 | VH3-53 FR2 | WVRQAPGKGLEWVS |
| 16 | VH3-53 FR3 | RFTISRDNSKNTLYLQMNSLRAEDT AVYYCAR |
| 17 | hJH4 FR4 | WGQGTLVTVSS |

TABLE 4

Light Chain Acceptor Sequences

| SEQ ID No. | Protein region | Sequence 123456789012345678901234567890123456789012 |
|---|---|---|
| 18 | O18 FR1 | DIQMTQSPSSLSASVGDRVTITC |
| 19 | O18 FR2 | WYQQKPGKAPKLLIY |
| 20 | O18 FR3 | GVPSRFSGSGSGTDFTFTISSLQPEDIATYYC |
| 21 | JK2 FR4 | FGQGTKLEIK |
| 22 | A14 FR1 | DVVMTQSPAFLSVTPGEKVTITC |
| 23 | A14 FR2 | WYQQKPDQAPKLLIK |
| 24 | A14 FR3 | GVPSRFSGSGSGTDFTFTISSLEAEDAATYYC |
| 25 | JK2 FR4 | FGQGTKLEIK |

The term "germline antibody gene" or "gene fragment" refers to an immunoglobulin sequence encoded by non-lymphoid cells that have not undergone the maturation process that leads to genetic rearrangement and mutation for expression of a particular immunoglobulin. (see, e.g., Shapiro et al. (2002) Crit. Rev. Immunol. 22(3): 183-200; Marchalonis et al. (2001) Adv. Exp. Med. Biol. 484:13-30). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

The term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

The term "humanized antibody" refers to antibodies that comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which non-human CDR sequences are introduced into human VH and VL sequences to replace the corresponding non-human framework (FR) sequences. For example, a "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. The term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In an embodiment, such mutations, however, will not be extensive. Usually, at least 80%, at least 85%, at least 90%, and at least 95% of the humanized antibody residues will correspond to those of the parental FR and CDR sequences. The term "consensus framework" refers to the framework region in the consensus immunoglobulin sequence. The term "consensus immunoglobulin sequence" refers to the sequence formed from the most frequently occurring amino acids (or nucleotides) in a family of related immunoglobulin sequences (See, e.g., Winnaker (1987) From Genes to Clones (Verlagsgesellschaft, Weinheim, Germany). A "consensus immunoglobulin sequence" can thus comprise a "consensus variable domain" and/or a "consensus constant domain". A "consensus variable domain" can in turn comprise one or more "consensus framework regions" and/or one or more "consensus CDRs". In a family of immunoglobulins, each position in the consensus sequence is occupied by the amino acid occurring most frequently at that position in the family. If two amino acids occur equally frequently, either can be included in the consensus sequence.

The term "Vernier" zone refers to a subset of framework residues that may adjust CDR structure and fine-tune the fit to antigen as described by Foote and Winter (1992) J. Mol. Biol. 224:487-499). Vernier zone residues form a layer underlying the CDRs and may impact on the structure of CDRs and the affinity of the antibody.

The term "multivalent binding protein" is used in this specification to denote a binding protein comprising two or more antigen binding sites. The multivalent binding protein is engineered to have the three or more antigen binding sites, and is generally not a naturally occurring antibody. The term "multispecific binding protein" refers to a binding protein capable of binding two or more related or unrelated targets. Dual variable domain (DVD) binding proteins, are binding proteins that comprise two or more antigen binding sites and are tetravalent or multivalent binding proteins. Such DVD binding proteins may be monospecific, i.e., capable of binding one antigen or multispecific, i.e., capable of binding two or more antigens. DVD binding proteins comprising two heavy chain DVD polypeptides and two light chain DVD polypeptides are referred to as DVD-Ig™ molecule. Each half of a DVD-Ig molecule comprises a heavy chain DVD-Ig polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. Pat. No. 7,612,181, which is incorporated herein by reference.

One aspect of the invention pertains to a DVD binding protein comprising binding proteins capable of binding human IL-1β. In another aspect, the DVD binding protein is capable of binding IL-1β and a second target. In one embodiment, the DVD binding protein is capable of binding IL-1α, and IL-1β.

The term "neutralizing" refers to neutralization of biological activity of a cytokine when a binding protein specifically binds the cytokine. In an embodiment, a neutralizing binding protein is a neutralizing antibody whose binding to hIL-1β results in inhibition of a biological activity of hIL-1β. Preferably the neutralizing binding protein binds hIL-1β and reduces a biologically activity of hIL-1β by at least about 20%, at least about 40%, at least about 60%, at least about 80%, at least about 85%, at least about 85%, at least about 90%, at least about 95%, or at least about 100%. Inhibition of a biological activity of hIL-1β by a neutralizing binding protein can be assessed by measuring one or more indicators of hIL-1β biological activity well known in the art.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. An epitope thus consists of the amino acid residues of a region of an antigen (or fragment thereof) known to bind to the complementary site on the specific binding partner. An antigenic fragment can contain more than one epitope. In certain embodiments, an antibody is said to specifically bind an antigen when it recognizes its target antigen in a complex mixture of proteins and/or macromolecules. Antibodies are said to "bind to the same epitope" if the antibodies cross-compete (one prevents the binding or modulating effect of the other). In addition structural definitions of epitopes (overlapping, similar, identical) are informative, but functional definitions are often more relevant as they encompass structural (binding) and functional (modulation, competition) parameters.

The term "surface plasmon resonance" refers to an optical phenomenon that allows for the analysis of real-time biospecific interactions by detection of alterations in protein concentrations within a biosensor matrix, for example using the BIACORä system (Biacore International AB, a GE Healthcare company, Uppsala, Sweden and Piscataway, N.J.). For further descriptions, see Jönsson, U. et al. (1993) Ann. Biol. Clin. 51:19-26; Jönsson, U. et al. (1991) BioTtechniques 11:620-627; Johnsson, B. et al. (1995) J. Mol. Recognit. 8:125-131; and Johnsson, B. et al. (1991) Anal. Biochem. 198:268-277.

The term "Kon" refers to the on rate constant for association of a binding protein (e.g., an antibody) to the antigen to form the, e.g., antibody/antigen complex as is known in the art. The "Kon" also is known by the terms "association rate constant," or "ka," as used interchangeably herein. This value indicating the binding rate of an antibody to its target antigen or the rate of complex formation between an antibody and antigen also is shown by the equation:

Antibody ("Ab")+Antigen ("Ag")→Ab-Ag.

The term "Koff" refers to the off rate constant for dissociation of a binding protein (e.g., an antibody) from the, e.g., antibody/antigen complex as is known in the art. The "Koff" also is known by the terms "dissociation rate constant" or "kd" as used interchangeably herein. This value indicates the dissociation rate of an antibody from its target antigen or separation of Ab-Ag complex over time into free antibody and antigen as shown by the equation below:

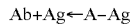

Ab+Ag←A-Ag

The terms "equilibrium dissociation constant" or "KD," as used interchangeably herein, refer to the value obtained in a titration measurement at equilibrium, or by dividing the dissociation rate constant (koff) by the association rate constant (kon). The association rate constant, the dissociation rate constant, and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIACORä (biomolecular interaction analysis) assay can be used (e.g., instrument available from Biacore International AB, a GE Healthcare company, Uppsala, Sweden). Additionally, a KinExA® (Kinetic Exclusion Assay) assay, available from Sapidyne Instruments (Boise, Id.) can also be used.

The term "labeled binding protein" refers to a protein with a label incorporated that provides for the identification of the binding protein. In one aspect, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{3}$H, $^{14}$C, $^{35}$S, $^{90}$Y, $^{99}$Tc, $^{111}$In, $^{125}$I, $^{131}$I, $^{177}$Lu, $^{166}$Ho and $^{153}$Sm); fluorescent labels (e.g., FITC, rhodamine, and lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, and epitope tags); and magnetic agents, such as gadolinium chelates.

The term "antibody conjugate" refers to a binding protein, such as an antibody, chemically linked to a second chemical moiety, such as a therapeutic or cytotoxic agent. The term "agent" denotes a chemical compound, a mixture of chemical compounds, a biological macromolecule, or an extract made from biological materials. In one aspect, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal", and "crystallized" refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giegé and Ducruix (1999) Chapter 1, In Crystallization of Nucleic Acids and Proteins, a Practical Approach, 2nd ed., (Ducruix and Giegé, eds.) (Oxford University Press, New York, 1999) pp. 1-16.

The term "polynucleotide" means a polymeric form of two or more nucleotides, either ribonucleotides or deoxynucleotides or a modified form of either type of nucleotide. The term includes single and double stranded forms of DNA or RNA but in an embodiment is double-stranded DNA.

The term "isolated polynucleotide" means a polynucleotide (e.g., of genomic, cDNA, or synthetic origin, or a combination thereof) that is not associated with all or a portion of a polynucleotide with which it is associated in nature, with which it is operably linked to in nature, or with which it occurs in nature as part of a larger sequence.

The term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a positioning of components such that they function in their intended manner. A control sequence "operably linked" to a coding sequence is ligated in such a way that expression of the coding sequence is achieved under conditions compatible with the control sequences. "Operably linked" sequences include expression control sequences that are contiguous with a nucleic acid of interest, expression control sequences that act in trans i.e., are located on a different nucleic acid molecule than a nucleic acid of interest but nevertheless exert control over the nucleic acid of interest, and expression control sequences that are located on the same nucleic acid molecule as, but at a distance from, a nucleic acid of interest. The term "expression control sequence" refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation" to any process by which exogenous DNA enters a host cell. Transformation may occur under natural or artificial conditions using various methods well known in the art for the insertion of foreign nucleic acid sequences into a prokaryotic or eukaryotic host cell, for example. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell") refers to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell". In one aspect, host cells include prokaryotic and eukaryotic cells selected from any of the Kingdoms of life. Eukaryotic cells include protist, fungal, plant and animal cells. In another embodiment, host cells include, but are not limited to, the prokaryotic cell line *Escherichia coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation and lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual, 2d ed. (Cold Spring Harbor Laboratory Press, Cold Spring Harbor, N.Y. 1989).

The term "transgenic organism" refers to an organism having cells that contain a transgene, wherein the transgene introduced into the organism (or an ancestor of the organism) expresses a polypeptide not naturally expressed in the organism. A "transgene" is a DNA construct that is stably and operably integrated into the genome of a cell from which a transgenic organism develops, directing the expression of an encoded gene product in one or more cell types or tissues of the transgenic organism.

The terms "regulate" and "modulate" are used interchangeably and refer to a change or an alteration in the activity of a molecule of interest (e.g., the biological activity of hIL-1$\beta$). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," is a compound capable of changing or altering an activity or function of a molecule of interest (e.g., the biological activity of hIL-1$\alpha$). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in PCT Publication No. WO01/83525.

The term "agonist" refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, IL-1β polypeptides or polypeptides, nucleic acids, carbohydrates, or any other molecules that bind to IL-1β.

The term "antagonist" or "inhibitor" refer to a modulator that, when contacted with a molecule of interest, causes a decrease in the magnitude of a certain activity or function of the molecule compared to the magnitude of the activity or function observed in the absence of the antagonist. Antagonists include those that block or modulate the biological or immunological activity of IL-1β. Antagonists and inhibitors of IL-1β may include, but are not limited to, proteins, nucleic acids, carbohydrates, or any other molecules that bind to IL-1β.

The term "effective amount" refers to the amount of a therapy that is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample" is used in its broadest sense. A "biological sample" includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

I. Antibodies That Bind Human IL-1α

One aspect of the present invention provides isolated monoclonal antibodies, or antigen-binding portions thereof, that bind to IL-1β with high affinity, have a slow off rate and have a high neutralizing capacity. A second aspect of the invention provides chimeric antibodies that bind IL-1β. A third aspect of the invention provides CDR grafted antibodies, or antigen-binding portions thereof, that bind IL-1β. A fourth aspect of the invention provides humanized antibodies, or antigen-binding portions thereof, that bind IL-1β. In an embodiment, the antibodies, or portions thereof, are isolated antibodies. In an embodiment, the antibodies of the invention are neutralizing human anti-IL-1β antibodies.

A. Methods Of Making Anti-IL-1β Antibodies

Antibodies of the present invention may be made by any of a number of techniques known in the art.

1. Anti-IL-1β Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow and Lane, Antibodies: A Laboratory Manual, 2d ed., (Cold Spring Harbor Laboratory Press, Cold Spring Harbor, 1988); Hammerling et al., eds., "Monoclonal Antibodies and T-Cell Hybridomas," In Research Monographs in Immunology, vol. 3 (J. L. Turk, General Editor) (Elsevier, N.Y., 1981) pp. 563-587. The term "monoclonal antibody" is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. Briefly, mice can be immunized with an IL-1β antigen. In a particular embodiment, the IL-1α antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. In an embodiment, if a polypeptide is being administered, the immunization schedule will involve two or more administrations of the polypeptide, spread out over several weeks.

After immunization of an animal with an IL-1β antigen, antibodies and/or antibody-producing cells may be obtained from the animal. An anti-IL-1β antibody-containing serum is obtained from the animal by bleeding or sacrificing the animal. The serum may be used as it is obtained from the animal, an immunoglobulin fraction may be obtained from the serum, or the anti-IL-1β antibodies may be purified from the serum. Serum or immunoglobulins obtained in this manner are polyclonal, thus having a heterogeneous array of properties.

Once an immune response is detected, e.g., antibodies specific for the antigen IL-1β are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding IL-1β. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. (See, e.g., Harlow and Lane, supra). In a particular embodiment, the myeloma cells do not secrete immunoglobulin polypeptides (a non-secretory cell line). After fusion and antibiotic selection, the hybridomas are screened using IL-1β, or a portion thereof, or a cell expressing IL-1β. In a particular embodiment, the initial screening is performed using an enzyme-linked immunoassay (ELISA) or a radioimmunoassay (RIA. An example of ELISA screening is provided in PCT Publication No. WO 00/37504.

Anti-IL-1β antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In an embodiment, the hybridomas are mouse hybridomas. In another embodiment, the hybridomas are produced in a non-human, non-mouse species such as rats, sheep, pigs, goats, cattle or horses. In yet another embodiment, the hybridomas are human hybridomas, in which a human non-secretory myeloma is fused with a human cell expressing an anti-IL-1β antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

2. Anti-IL-1β Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052, PCT Publication No. WO 92/02551 and Babcook et al. (1996) Proc. Natl. Acad. Sci. USA 93:7843-7848. In this method, single cells secreting antibodies of interest, e.g., lymphocytes derived from an immunized animal, are screened using an antigen-specific hemolytic plaque assay, wherein the antigen IL-1β, or a fragment thereof, is coupled to sheep red blood cells using a linker, such as biotin, and used to identify single cells that secrete antibodies with specificity for IL-1β. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to IL-1β. The amplified immunoglobulin sequences further can be manipulated in vitro, such as by in vitro affinity maturation methods such as those described in PCT Publication Nos. WO 97/29131 and WO 00/56772.

3. Anti-IL-1β Monoclonal Antibodies Using Transgenic Animals

In another embodiment of the instant invention, antibodies are produced by immunizing a non-human animal comprising some, or all, of the human immunoglobulin locus with an IL-1β antigen. In an embodiment, the non-human animal is a XENOMOUSE® transgenic mouse, an engineered mouse strain that comprises large fragments of the human immunoglobulin loci and is deficient in mouse antibody production. See, e.g., Green et al. (1994) Nature Genet. 7:13 21 and U.S. Pat. Nos. 5,916,771; 5,939,598; 5,985,615; 5,998,209; 6,075,181; 6,091,001; 6,114,598 and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germline configuration YAC fragments of the human heavy chain loci and x light chain loci. See, Mendez et al. (1997) Nature Genet. 15:146-156 and Green and Jakobovits (1998) J. Exp. Med. 188:483-495.

4. Anti-IL-1β Monoclonal Antibodies Using Recombinant Antibody Libraries

In vitro methods also can be used to make the antibodies of the invention, wherein an antibody library is screened to identify an antibody having the desired binding specificity. Methods for such screening of recombinant antibody libraries are well known in the art and include methods described in, for example, U.S. Pat. No. 5,223,409; PCT Publication Nos. WO 92/18619, WO 91/17271, WO 92/20791, WO 92/15679, WO 93/01288, WO 92/01047, WO 92/09690; WO 97/29131; Fuchs et al. (1991) Bio/Technology 9:1369-1372; Hay et al. (1992) Hum. Antibod. Hybridomas 3:81-85; Huse et al. (1989) Science 246:1275-1281; McCafferty et al. (1990) Nature 348:552-554; Griffiths et al. (1993) EMBO J. 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrard et al. (1991) Bio/Technology 9:1373-1377; Hoogenboom et al. (1991) Nucl. Acids Res. 19:4133-4137; and Barbas et al. (1991) Proc. Natl. Acad. Sci. USA 88:7978-7982, and U.S. Patent Publication No. 2003/0186374.

The recombinant antibody library may be from a subject immunized with IL-1β, or a portion of IL-1β. Alternatively, the recombinant antibody library may be from a naïve subject, i.e., one who has not been immunized with IL-1β, such as a human antibody library from a human subject who has not been immunized with human IL-1β. Antibodies of the invention are selected by screening the recombinant antibody library with the peptide comprising human IL-1β to thereby select those antibodies that recognize IL-1β. Methods for conducting such screening and selection are well known in the art, such as described in the references in the preceding paragraph. To select antibodies of the invention having particular binding affinities for hIL-1β, such as those that dissociate from human IL-1β with a particular $k_{off}$ rate constant, the art-known method of surface plasmon resonance can be used to select antibodies having the desired $k_{off}$ rate constant. To select antibodies of the invention having a particular neutralizing activity for hIL-1β, such as those with a particular $IC_{50}$, standard methods known in the art for assessing the inhibition of hIL-1β activity may be used.

In one aspect, the invention pertains to an isolated antibody, or an antigen-binding portion thereof, that binds human IL-1β. In a particular embodiment, the antibody is a neutralizing antibody. In various embodiments, the antibody is a recombinant antibody or a monoclonal antibody.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkmann et al. (1995) J. Immunol. Methods 182:41-50; Ames et al. (1995) J. Immunol. Methods 184:177-186; Kettleborough et al. (1994) Eur. J. Immunol. 24:952-958; Persic et al. (1997) Gene 187 9-18;

Burton et al. (1994) Adv. Immunol. 57:191-280; PCT Application No. PCT/GB91/01134; PCT Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

After phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail herein. For example, techniques to recombinantly produce Fab, Fab' and F(ab')2 fragments can also be employed using methods known in the art such as those disclosed in PCT Publication No. WO 92/22324; Mullinax et al. (1992) BioTechniques 12(6):864-869; Sawai et al. (1995) Am. J. Reprod. Immunol. 34:26-34; and Better et al. (1988) Science 240:1041-1043. Examples of techniques that can be used to produce single-chain Fvs and antibodies include those described in U.S. Pat. Nos. 4,946,778 and 5,258,498; Huston et al. (1991) Methods Enzymol. 203:46-88; Shu et al. (1993) Proc. Natl. Acad. Sci. USA 90:7995-7999; and Skerra et al. (1988) Science 240:1038-1041.

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 and in Roberts and Szostak (1997) Proc. Natl. Acad. Sci. USA 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed U.S. Pat. No. 6,699,658.

B. Production Of Recombinant IL-1β Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in Kaufman and Sharp (1982) J. Mol. Biol. 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other human IL-1β by crosslinking an antibody of the invention to a second antibody by standard chemical crosslinking methods.

In a particular system for recombinant expression of an antibody of the invention, or antigen-binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

1. Anti IL-1β Antibodies

Table 5 provides the amino acid sequences of VH and VL regions of the mouse anti-hIL-1β monoclonal antibody (mAb) of the invention.

TABLE 5

Amino Acid Sequences of VH and VL Regions of Mouse Anti-Human IL-1β

| SEQ ID No. | Protein region | Amino Acid Sequence 12345678901234567890123456789 |
|---|---|---|
| 26 | 1B12.4H4 VH | QVHLKESGPGLVAPSQSLSITCTVSGFSLT DYGVSWIRQPPGKGLEWLGLIWGGGDTYYN SPLKSRLSIRKDNSKSQVFLKMNSLQTDDT AVYYCAKQRTLWGYDLYGMDYWGQGTSVTV SS |
| 27 | 1B12.4H4 VL | ETTVTQSPASLSMAIGEKVTIRCITSTDID VDMNWYQQKPGEPPKLLISQGNTLRPGVPS RFSSSGSGTDFVFIIENMLSEDVADYYCLQ SDNLPLTFGAGTKLELK |

2. Anti IL-1β Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art and are discussed in the Examples. See, e.g., Morrison (1985) Science 229:1202-1207; Oi et al. (1986) BioTechniques 4:214-221; Gillies et al. (1989) J. Immunol. Methods 125:191-202; and U.S. Pat. Nos. 5,807,715; 4,816,567; and 4,816,397. In addition, techniques developed for the production of "chimeric antibodies" by splicing genes from a mouse antibody molecule of appropriate antigen specificity together with genes from a human antibody molecule of appropriate biological activity can be used (Morrison et al. (1984) Proc. Natl. Acad. Sci. USA 81:6851-6855; Neuberger et al. (1984) Nature 312:604-608; and Takeda et al. (1985) Nature 314:452-454).

3. Anti-IL-1β CDR-Grafted Antibodies

CDR-grafted antibodies of the invention comprise heavy and light chain variable region sequences from a human antibody wherein one or more of the CDR regions of VH and/or VL are replaced with CDR sequences of the murine antibodies of the invention. A framework sequence from any human antibody may serve as the template for CDR grafting. However, straight chain replacement onto such a framework often leads to some loss of binding affinity to the antigen. The more homologous a human antibody is to the original murine antibody, the less likely the possibility that combining the murine CDRs with the human framework will introduce distortions in the CDRs that could reduce affinity. Therefore, in an embodiment, the human variable framework that is chosen to replace the murine variable framework apart from the CDRs have at least about 65%, at least about 70%, at least about 75%, at least about 80%, at least about 85%, at least about 90%, at least about 95%, about 100%, sequence identity with the murine antibody variable region framework. Methods for producing CDR-grafted antibodies are known in the art and described in detail along with humanization of such CDR-grafted antibodies in the Examples (see also, EP Patent No. EP 0 239 400; PCT Publication No. WO 91/09967; U.S. Pat. Nos. 5,225,539; 5,530,101; and 5,585,089); veneering or resurfacing (EP Patent Nos. EP 0 592 106 and EP 0 519 596; Padlan (1991) Mol. Immunol. 28(4/5):489-498; Studnicka et al. (1994) Protein Eng. 7(6):805-814; Roguska et al. (1994) Proc. Natl. Acad. Sci. USA 91:969-973), and chain shuffling (U.S. Pat. No. 5,565,352).

4. Anti IL-1β Humanized Antibodies

Humanized antibodies are antibody molecules that have one or more complementarity determining regions (CDRs) from a non-human species and framework regions from a human immunoglobulin molecule. Known human Ig sequences are disclosed, e.g., www.ncbi.nlm.nih.gov/entrez-/query.fcgi; www.atcc.org/phage/hdb.html; www.sciquest.com/; www.abcam.com/; www.antibodyresource.com/onlinecomp.html; www.public.iastate.eduL.about. pedro/research_tools.html; www.mgen.uni-heidelberg.de/SD/IT/IT.html; www.whfreeman.com/immunology/CH-05/kuby05.htm; www.library.thinkquest.org/12429/Immune/Antibody.html; www.hhmi.org/grants/lectures/1996/vlab/; www.path.cam.ac.uk/.about.mrc7/m-ikeimages.html; www.antibodyresource.com/; mcb.harvard.edu/BioLinks/Immuno-logy.html.www.immunologylink.com/; pathbox.wustl.edu/. about.hcenter/index.-html; www.biotech.ufl.edu/.about.hcl/; www.pebio.com/pa/340913/340913.html-; www.nal.usda.gov/awic/pubs/antibody/; www.m.ehime-u.acjp/.about. yasuhito-/Elisa.html; www.biodesign.com/table.asp; www.icnet.uk/axp/facs/davies/lin-ks.html; www.biotech.ufl.edu/.about.fccl/protocol.html; www.isac-net.org/sites_ geo.html; aximtl.imt.uni-marburg.de/.about.rek/AEP-Start.html; baserv.uci.kun.nl/.about.jraats/linksl.html; www.recab.uni-hd.de/immuno.bme.nwu.edu/; www.mrc-cpe.cam.ac.uk/imt-doc/pu-blic/INTRO.html; www.ibt.unam.mx/V_mice.html; imgt.cnusc.fr:8104/; www.biochem.ucl.ac.uk/.about.martin/abs/index.html; antibody.bath.ac.uk/; abgen.cvm.tamu.edu/lab/wwwabgen.html; www.unizh.ch/.about.honegger/AHOsem-inar/Slide01.html; www.cryst.bbk.ac.uk/.about.ubcg07s/; www.nimr.mrc.ac.uk/CC/ccaewg/ccaewg.htm; www.path.cam.ac.uk/.about.mrc7/h-umanisation/TAHHP.html; www.ibt.unam.mx/vinstructure/stataim.html; www.biosci.missouri.edu/smithgp/index.html; www.cryst.bioc.cam.ac.uk/.abo-ut.finolina/Web-pages/Pept/spottech.html; www.jerini.de/fr oducts.htm; www.patents.ibm.com/ibm.html.Kabat et al., Sequences of Proteins of Immunological Interest, U.S. Dept. Health (1983). Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, for example, improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089 and Riechmann et al. (1988) Nature 332:323-327). Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al. (1986) Nature 321:522-525; Verhoeyen et al. (1988) Science 239:1534-1536, Sims et al. (1993) J. Immunol. 151: 2296-2308; Chothia and Lesk (1987) J. Mol. Biol. 196:901-917; Carter et al. (1992) Proc. Natl. Acad. Sci. USA 89:4285-4289; Presta et al. (1993) J. Immunol. 151:2623-2632; Padlan (1991) Mol. Immunol. 28(4/5):489-498; Studnicka et al. (1994) Protein Eng. 7(6): 805-814; Roguska. et al. (1994) Proc. Natl. Acad. Sci. USA 91:969-973; PCT Publication Nos. WO 91/09967, WO 99/06834 (PCT/US98/16280), WO 97/20032 (PCT/US96/18978), WO 92/11272 (PCT/US91/09630), WO 92/03461 (PCT/US91/05939), WO 94/18219 (PCT/US94/01234), WO 92/01047 (PCT/GB91/01134), WO 93/06213 (PCT/GB92/01755), WO 90/14443, WO 90/14424, and WO 90/14430; European Publication Nos. EP 0592106, EP 0519596, and EP 0239400; U.S. Pat. Nos. 5,565,332; 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

C. Production of Antibodies and Antibody-Producing Cell Lines

In an embodiment, anti-IL-1β antibodies of the present invention, exhibit a high capacity to reduce or to neutralize IL-1β activity, e.g., as assessed by any one of several in vitro and in vivo assays known in the art. In an embodiment, anti-IL-1β antibodies of the present invention, also exhibit a high capacity to reduce or to neutralize IL-1β activity In particular embodiments, the isolated antibody, or antigen-binding portion thereof, binds human IL-1β, wherein the antibody, or antigen-binding portion thereof, dissociates from human IL-1β with a $k_{off}$ rate constant of about $0.1s^{-1}$ or less, as determined by surface plasmon resonance, or which inhibits human IL-1β activity with an $IC_{50}$ of about $1\times10^{-6}$M or less. Alternatively, the antibody, or an antigen-binding portion thereof, may dissociate from human IL-1β with a $k_{off}$ rate constant of about $1\times10^{-2}s^{-1}$ or less, as determined by surface plasmon resonance, or may inhibit human IL-1β activity with an $IC_{50}$ of about $1\times10^{-7}$M or less. Alternatively, the antibody, or an antigen-binding portion thereof, may dissociate from human IL-1β with a $k_{off}$ rate constant of about $1\times10^{-3}s^{-1}$ or less, as determined by surface plasmon resonance, or may inhibit human IL-1β with an $IC_{50}$ of about $1\times10^{-8}$M or less. Alternatively, the antibody, or an antigen-binding portion thereof, may dissociate from human IL-1β with a $k_{off}$ rate constant of about $1\times10^{-4}s^{-1}$ or less, as determined by surface plasmon resonance, or may inhibit IL-1β activity with an $IC_{50}$ of about $1\times10^{-9}$M or less. Alternatively, the antibody, or an antigen-binding portion thereof, may dissociate from human IL-1β with a $k_{off}$ rate constant of about $1\times10^{-5}s^{-1}$ or less, as determined by surface plasmon resonance, or may inhibit IL-1β activity with an $IC_{50}$ of about $1\times10^{-10}$M or less. Alternatively, the antibody, or an antigen-binding portion thereof, may dissociate from human IL-1β with a $k_{off}$ rate constant of about $1\times10^{-5}s^{-1}$ or less, as determined by surface plasmon resonance, or may inhibit human IL-1β activity with an $IC_{50}$ of about $1\times10^{-11}$M or less.

In certain embodiments, the antibody comprises a heavy chain constant region, such as an IgG1, IgG2, IgG3, IgG4, IgA, IgE, IgM or IgD constant region. In an embodiment, the heavy chain constant region is an IgG1 heavy chain constant region or an IgG4 heavy chain constant region. Furthermore, the antibody can comprise a light chain constant region, either a kappa light chain constant region or a lambda light chain constant region. In an embodiment, the antibody comprises a kappa light chain constant region. Alternatively, the antigen binding portion can be, for example, a Fab fragment or a single chain Fv fragment.

Replacements of amino acid residues in the Fc portion to alter antibody effector function are known in the art (U.S. Pat. Nos. 5,648,260 and 5,624,821). The Fc portion of an antibody mediates several important effector functions, e.g., cytokine induction, antibody dependent cell-mediated cytotoxicity (ADCC), phagocytosis, complement dependent cytotoxicity (CDC) and half-life/clearance rate of antibody and antigen-antibody complexes. In some cases these effector functions are desirable for a therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment provides a labeled binding protein wherein an antibody, or antigen binding portion thereof, of the invention is derivatized or linked to another functional molecule (e.g., another peptide or protein). For example, a labeled binding protein of the invention can be derived by functionally linking an antibody, or antigen binding portion thereof, of the invention (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody, or antigen binding portion thereof, with another molecule (such as a streptavidin core region or a polyhistidine tag).

Useful detectable agents with which an antibody, or antigen binding portion thereof, of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized binding protein. In an embodiment, the invention relates to crystals of whole anti-IL-1β antibodies and fragments thereof as disclosed herein, and formulations and compositions comprising such crystals. In one embodiment the crystallized binding protein has a greater half-life in vivo than the soluble counterpart of the binding protein. In another embodiment the binding protein retains biological activity after crystallization.

Crystallized binding protein of the invention may be produced according methods known in the art and as disclosed in PCT Publication No. WO 02/72636.

Another embodiment of the invention provides a glycosylated binding protein wherein an antibody, or antigen-binding portion thereof, comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Protein glycosylation depends on the amino acid sequence of the protein of interest, as well as the host cell in which the protein is expressed. Different organisms may produce different glycosylation enzymes (e.g., glycosyltransferases and glycosidases), and have different substrates (e.g., nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. In an embodiment, the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. Pat. Nos. 7,449,308 and 7,029,872).

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. In an embodiment, the protein having a particularly selected novel glycosylation pattern exhibits improved or altered biological properties.

D. Uses of Anti-IL-1β Antibodies

Given their ability to bind to human IL-1β, the binding proteins, e.g., anti-IL-1β antibodies and antigen-binding portions thereof, according to the invention can be used to detect IL-1β (e.g., in a biological sample, such as whole blood, serum, plasma, urine, saliva, tissue sample) using any of the vast array of antibody-based immunodetection systems available in the art. Such immunodetection systems include, but are not limited to, immunoprecipitation, immunblotting (Western blot), enzyme-linked immunsorbent assay (ELISA), radioimmunoassay (RIA), tissue immunohistochemistry, surface plasmon resonance (SPR), sandwich immunoassay, antibody-based affinity methods (e.g., affinity beads, affinity columns), immunocompetition assay, immunochip assay (binding protein attached to a silicon chip), and fluorescence activated cell sorting (FACS). For some immunodetection systems, an IL-1β binding protein (or binding portion thereof) of the invention (or portion thereof) is attached to a solid substrate using methods available in the art for attaching antibody molecules to the same solid substrate so that the attached binding protein retains its ability to bind human IL-1β during use in the particular immunodetection system. Such solid substrates include, but are not limited to, a cellulose-based filter paper (e.g., cellulose, nitrocellulose, cellulose acetate), a nylon filter, a plastic surface (e.g., microtiter plate, antibody dip stick), a glass substrate (e.g., filters, beads, slides, glass wool), a polymeric particle (e.g., agarose, polyacrylamide), and a silicon chip. For example, an immunodetection system may be used in a method for detecting the presence of IL-1β in a sample in vitro (e.g., a biological sample, such as whole blood, serum, plasma, tissue, urine, saliva, tissue biopsy). Such a method can be used to diagnose a disease or disorder, e.g., an immune cell-associated disorder. The method includes: (i) contacting a test sample or a control sample with an IL-1β binding protein, or IL-1β binding portion thereof, as described herein; and (ii) detecting formation of a complex between the anti-IL-1β binding protein (or binding portion thereof) and IL-1β in the test sample or in the control sample, wherein a statistically significant change in the formation of the complex in the test sample relative to the control sample (or relative to formation of the complex in another test sample taken at an earlier time point) is indicative of the presence of IL-1β in the sample.

As another example, a method may be employed for detecting the presence of human IL-1β in vivo (e.g., in vivo imaging in a subject). The method can be used to diagnose a disease or disorder, e.g., an IL-1β-associated disorder. The method includes: (i) administering an IL-1β binding protein, or IL-1β binding portion thereof, as described herein to a test subject or a control subject under conditions that allow binding of the binding protein, or IL-1β binding portion thereof, to IL-1β; and (ii) detecting formation of a complex between the binding protein, or binding portion thereof, and IL-1β, wherein a statistically significant change in the formation of the complex in the test subject relative to the control subject, or relative to formation of the complex in the test subject at an earlier time point, is indicative of the presence of IL-1β. Methods for detecting IL-1β in a sample (e.g., a biological sample) according to the invention comprise contacting a sample with an IL-1β binding protein (or IL-1β binding portion thereof) described herein and detecting either the binding protein (or binding portion thereof) bound to IL-1β or unbound binding protein (or unbound binding portion thereof) to thereby detect IL-1β in the sample. The binding protein (or portion thereof) is directly or indirectly labeled with a detectable substance to facilitate detection of the bound or unbound binding protein (or portion thereof). Such detectable substances are known in the art and, by way of non-limiting example, include various enzymes, prosthetic groups, fluorescent materials, luminescent materials, and radioactive materials. Examples of suitable enzymes include horseradish peroxidase, alkaline phosphatase, β-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride, or phycoerythrin. An example of a luminescent material includes luminol. Examples of suitable radioactive materials include the radioisotopes 3H, 14C, 35S, 90Y, 99Tc, 111In, 125I, 131I, 177Lu, 166Ho, and 153Sm. Alternatively to labeling the binding protein, human IL-1β can be assayed in a sample (e.g., a biological fluid) by a competition immunoassay utilizing recombinant human (rh) IL-1β standards labeled with a detectable substance and an unlabeled IL-1β binding protein (or IL-1β binding portion thereof). In this assay, the sample, the labeled rh IL-1β standards, and the IL-1β binding protein are combined and the amount of labeled rh IL-1β standard bound to the unlabeled binding protein is determined. The amount of human IL-1β in the sample is inversely proportional to the amount of labeled rh IL-1β standard bound to the IL-1β binding protein. Similarly, human IL-1β can also be assayed in a sample by a competition immunoassay utilizing rh IL-1β standards labeled with a detectable substance and an unlabeled IL-1β binding protein described herein.

In an embodiment, the IL-1β binding proteins, and IL-1β binding portions thereof, according to the invention are capable of neutralizing IL-1β activity both in vitro and in vivo. Accordingly, such binding proteins, and IL-1β binding portions thereof, of the invention can be used to inhibit IL-1β activity, e.g., in a cell culture containing IL-1β, in human subjects, or in other mammalian subjects having IL-1β with which a binding protein of the invention cross-reacts. In one embodiment, the invention provides a method for inhibiting IL-1β activity comprising contacting IL-1β with a binding protein, or binding portion thereof, of the invention such that IL-1β activity is inhibited. For example, in a cell culture containing or suspected of containing IL-1β, a binding protein (or binding portion thereof) of the invention can be added to the culture medium to inhibit IL-1β activity in the culture.

In another embodiment, the invention provides a method for reducing IL-1β activity in a subject, advantageously from a subject suffering from a disease or disorder in which IL-1β activity is detrimental. The invention provides methods for reducing IL-1β activity in a subject suffering from such a disease or disorder, which method comprises administering to the subject a binding protein or antigen binding portion thereof, of the invention such that IL-1β activity in the subject is reduced. In an embodiment, the IL-1β is human IL-1β, and the subject is a human subject. Alternatively, the subject can be a mammal expressing an IL-1β to which a binding protein of the invention is capable of binding. Still further the subject can be a mammal into which IL-1β has been introduced (e.g., by administration of IL-1β or by expression of an IL-1β transgene). A binding protein of the invention can be administered to a human subject for therapeutic purposes. Moreover, a binding protein of the invention can be administered to a non-human mammal expressing an IL-1β with which the binding protein is capable of binding for veterinary purposes or as an animal model of human disease. Regarding the latter, such animal models may be useful for evaluating the therapeutic efficacy of antibodies of the invention (e.g., testing of dosages and time courses of administration).

The term "a disorder in which IL-1β activity is detrimental" includes diseases and other disorders in which the presence of IL-1β in a subject suffering from the disorder has been shown to be or is suspected of being either responsible for the pathophysiology of the disorder or a factor that contributes to a worsening of the disorder. Accordingly, a disorder in which IL-1β activity is detrimental is a disorder in which reduction of IL-1β activity is expected to alleviate the symptoms and/or progression of the disorder. Such disorders may be evidenced, for example, by an increase in the concentration of IL-1β in a biological fluid of a subject suffering from the disorder (e.g., an increase in the concentration of IL-1β in serum, plasma, synovial fluid, etc. of the subject), which can be detected, for example, using an anti-IL-1β binding protein as described above. Non-limiting examples of disorders that can be treated with the binding proteins of the invention include those disorders discussed in the section below pertaining to pharmaceutical compositions of the binding proteins of the invention.

E. Pharmaceutical Compositions

The invention also provides pharmaceutical compositions comprising a binding protein (e.g., an antibody, or antigen-binding portion thereof) of the invention and a pharmaceutically acceptable carrier. The pharmaceutical compositions comprising binding proteins of the invention are for use in, but not limited to, diagnosing, detecting, or monitoring a disorder, in preventing, treating, inhibiting, managing, or ameliorating of a disorder or one or more symptoms thereof, and/or in research. In a specific embodiment, a composition comprises one or more binding proteins of the invention. In another embodiment, the pharmaceutical composition comprises one or more binding proteins of the invention and one or more prophylactic or therapeutic agents other than the one or more binding proteins of the invention for treating a disorder in which IL-1β activity is detrimental. In particular, the prophylactic or therapeutic agents are known to be useful for, or have been, or are currently being used in the prevention, treatment, management, or amelioration of a disorder, or one or more symptoms thereof. In accordance with these embodiments, the composition may further comprise of a carrier, diluent or excipient.

The binding proteins of the invention can be incorporated into pharmaceutical compositions suitable for administration to a subject. Typically, the pharmaceutical composition comprises a binding protein (e.g., an antibody or antigen binding portion thereof) of the invention and a pharmaceutically acceptable carrier. The term "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. It may be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antigen binding portion thereof.

Various delivery systems are known and can be used to administer one or more binding proteins of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu (1987) J. Biol. Chem. 262:4429-4432), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In one embodiment, a binding protein of the invention, combination therapy, or a composition of the invention is administered using Alkermes AIR® pulmonary drug delivery technology (Alkermes, Inc., Cambridge, Mass.). The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment, for example, by local infusion, by injection, or by means of an implant. An implant may be porous or non-porous material, including membranes and matrices, such as sialastic membranes, polymers, fibrous matrices (e.g., TISSUEL®), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than a binding protein of the invention of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see Langer (1990) Science 249:1527-1533; Sefton (1987) CRC Crit. Rev. Biomed. Eng. 14:201-240; Buchwald et al. (1980) Surgery 88:507-516; Saudek et al. (1989) N. Engl. J. Med. 321:574-579). In another embodiment, polymeric materials can be used to achieve controlled or sustained release of the therapies of the invention (see, e.g., Medical Applications of Controlled Release, (Langer and Wise, eds.) (CRC Press, Inc., Boca Raton, 1984); Controlled Drug Bioavailability, Drug Product Design and Performance, (Smolen and Ball, eds.) (Wiley, New York, 1984); Langer and Peppas (1983) J. Macromol. Sci. Rev. Macromol. Chem. Phys. C23:61-126; see also Levy et al. (1985) Science 228:190-192; During et al. (1989) Ann. Neurol. 25:351-356; Howard et al. (1989) J. Neurosurg. 71:105-112); U.S. Pat. Nos. 5,679,377; 5,916,597; 5,912,015; 5,989,463; and 5,128,326; and PCT Publication Nos. WO 99/15154 and WO 99/20253. Examples of polymers used in sustained release formulations include, but are not limited to, poly(2-hydroxy ethyl methacrylate), poly (methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In an embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, J. M., Chapter 6, In Medical Applications of Controlled Release, Vol. II, Applications and Evaluation, (Langer and Wise, eds.)(CRC Press, Inc., Boca Raton, 1984), pp. 115-138).

Controlled release systems are discussed in the review by Langer (1990) Science 249:1527-1533. Any technique known to one of skill in the art can be used to produce sustained release formulations comprising one or more therapeutic agents of the invention. See, e.g., U.S. Pat. No. 4,526,938; and PCT Publication Nos. WO 91/05548 and WO 96/20698; and Ning et al. (1996) Radiother. Oncol. 39:179-189; Song et al. (1996) PDA J. Pharm. Sci. Technol. 50:372-377; Cleek et al. (1997) Proceed Int'l. Symp. Control. Rel. Bioact. Mater. 24:853-854; and Lam et al. (1997) Proceed. Int'l. Symp. Control Rel. Bioact. Mater. 24:759-760.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al. (1991) Proc. Natl. Acad. Sci. USA 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., (Mack Publishing Co., Easton, Pa., 1995). For non-sprayable topical dosage forms, viscous to semisolid or solid forms comprising a carrier or one or more excipients compatible with topical application and having a dynamic viscosity preferably greater than water are typically employed. Other suitable formulations include, without limitation, suspensions, powders, liniments, salves, and the like. In an embodiment, such formulations are sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, for example, in combination with a solid or liquid inert carrier, is packaged in a mixture with a pressurized volatile (e.g., a gaseous propellant, such as FREON®) or in a squeeze bottle. Moisturizers or humectants can also be added to pharmaceutical compositions and dosage forms if desired. Examples of such additional ingredients are well-known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244, WO 97/32572, WO 97/44013, WO 98/31346, and WO 99/66903. In a specific embodiment, an antibody of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. In an embodiment, one or more of the prophylactic or therapeutic agents or pharmaceutical compositions of the invention is supplied as a dry sterile lyophilized powder in a hermetically sealed container at a unit dosage of at least about 5 mg, at least about 10 mg, at least about 15 mg, at least about 25 mg, at least about 35 mg, at least about 45 mg, at least about 50 mg, at least about 75 mg, or at least about 100 mg. The lyophilized prophylactic or therapeutic agents or pharmaceutical compositions of the invention should be stored at between about 2° C. and about 8° C. in its original container and the prophylactic or therapeutic agents, or pharmaceutical compositions of the invention should be administered within 1 week, within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. In an embodiment, the liquid form of the administered composition is supplied in a hermetically sealed container at least about 0.25 mg/ml, at least about 0.5 mg/ml, at least about 1 mg/ml, at least about 2.5 mg/ml, at least about 5 mg/ml, at least about 8 mg/ml, at least about 10 mg/ml, at least about 15 mg/kg, at least about 25 mg/ml, at least about 50 mg/ml, at least about 75 mg/ml or at least about 100 mg/ml. The liquid form should be stored at between about 2° C. and about 8° C. in its original container.

The binding proteins of the invention can be incorporated into a pharmaceutical composition suitable for parenteral administration. In one aspect, the binding proteins are prepared as an injectable solution containing about 0.1 to about 250 mg/ml antibody. The injectable solution can be composed of either a liquid or lyophilized dosage form in a flint or amber vial, ampoule or pre-filled syringe. The buffer can be L-histidine (about 1 to about 50 mM), optimally about 5 to about 10 mM, at pH 5.0 to 7.0 (optimally about pH 6.0). Other suitable buffers include but are not limited to, sodium succinate, sodium citrate, sodium phosphate or potassium phosphate. Sodium chloride can be used to modify the toxicity of the solution at a concentration of about 0 to about 300 mM (e.g., about 150 mM for a liquid dosage form). Cryoprotectants can be included for a lyophilized dosage form, principally about 0 to about 10% sucrose (e.g., about 0.5 to about 1.0%). Other suitable cryoprotectants include trehalose and lactose. Bulking agents can be included for a lyophilized dosage form, principally about 1 to about 10% mannitol (e.g., about 2 to about 4%). Stabilizers can be used in both liquid and lyophilized dosage forms, principally about 1 to about 50 mM L-Methionine (optimally about 5 to about 10 mM). Other suitable bulking agents include glycine, arginine, can be included as about 0 to about 0.05% polysorbate-80 (optimally about 0.005 to about 0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The particular form depends on the intended mode of administration and therapeutic application. Typical compositions are in the form of injectable or infusible solutions, such as compositions similar to those used for passive immunization of humans with other antibodies. The mode of administration is parenteral (e.g., intravenous, subcutaneous, intraperitoneal, intramuscular). In an embodiment, the antibody is administered by intravenous infusion or injection. In another embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (e.g., antibody or antigen binding portion thereof) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the exemplary methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The binding proteins of the present invention can be administered by a variety of methods known in the art, although for many therapeutic applications, an exemplary route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978).

In certain embodiments, an antibody, or antigen binding portion thereof, of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, a bindin protein (e.g., an antibody) or antigen binding portion thereof, of the invention is coformulated with and/or coadministered with one or more additional therapeutic agents that are useful for treating disorders in which IL-1β activity is detrimental. For example, an anti-hiL-1β binding protein or antigen binding portion thereof, of the invention may be coformulated and/or coadministered with one or more additional antibodies that bind other targets (e.g., antibodies that bind other cytokines or that bind cell surface molecules). Furthermore, one or more binding proteins of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an IL-1β binding protein, or IL-1β-binding portion thereof, as described herein is linked to a half-life extending vehicle known in the art. Such vehicles include, but are not limited to, the Fc domain, polyethylene glycol, and dextran. Such vehicles are described, e.g., in U.S. Pat. No. 6,660,843 and published PCT Publication No. WO 99/25044.

In a specific embodiment, nucleic acid molecules comprising nucleotide sequences encoding one or more polypeptides of a binding protein of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded binding polypeptide(s) of a binding protein or prophylactic or therapeutic agent of the invention that mediates a prophylactic or therapeutic effect.

Any of the methods for gene therapy available in the art can be used according to the present invention. For general reviews of the methods of gene therapy, see Goldspiel et al. (1993) Clin. Pharm. 12:488-505; Wu and Wu (1991) Biotherapy 3:87-95; Tolstoshev (1993) Ann. Rev. Pharmacol. Toxicol. 32:573-596; Mulligan (1993) Science 260:926-932; and Morgan and Anderson (1993) Ann. Rev. Biochem. 62:191-217; Robinson, C. (1993) Trends Biotechnol. 11(5): 155. Methods commonly known in the art of recombinant DNA technology which can be used are described in Ausubel et al. (eds.), Current Protocols in Molecular Biology (John Wiley & Sons, New York, 1993); and Kriegler, Gene Transfer and Expression, A Laboratory Manual, (Stockton Press, New York, 1990). Detailed descriptions of various methods of gene therapy are disclosed in US 2005/0042664.

IL-1β plays a critical role in the pathology associated with a variety of diseases involving immune and inflammatory elements. These diseases include, but are not limited to, Acquired Immunodeficiency Disease Syndrome; Acquired Immunodeficiency Related Diseases; acquired pernicious anaemia; acute coronary syndromes; acute and chronic pain (different forms of pain); acute idiopathic polyneuritis; acute immune disease associated with organ transplantation; acute or chronic immune disease associated with organ transplantation; acute inflammatory demyelinating polyradiculoneuropathy; acute ischemia; acute liver disease; acute rheumatic fever; acute transverse myelitis; Addison's disease; adult (acute) respiratory distress syndrome; adult Still's disease; alcoholic cirrhosis; alcohol-induced liver injury; allergic diseases; allergy; alopecia; alopecia areata; Alzheimer's disease; anaphylaxis; ankylosing spondylitis; ankylosing spondylitis associated lung disease; anti-phospholipid antibody syndrome; aplastic anemia; arteriosclerosis; arthropathy; asthma; atheromatous disease/arteriosclerosis; atherosclerosis; atopic allergy; atopic eczema; atopic dermatitis; atrophic autoimmune hypothyroidism; autoimmune bullous disease; autoimmune dermatitis; autoimmune diabetes; autoimmune disorder associated with *streptococcus* infection; autoimmune enteropathy; autoimmune haemolytic anaemia; autoimmune hepatitis; autoimmune hearing loss; autoimmune lymphoproliferative syndrome (ALPS); autoimmune mediated hypoglycaemia; autoimmune myocarditis; autoimmune neutropenia; autoimmune premature ovarian failure; autoimmune thrombocytopenia (AITP); autoimmune thyroid disease; autoimmune uveitis; bronchiolitis obliterans; Behçet's disease; blepharitis; bronchiectasis; bullous pemphigoid; cachexia; cardiovascular disease; catastrophic antiphospholipid syndrome; celiac disease; cervical spondylosis; chlamydia; choleosatatis; chronic active hepatitis; chronic eosinophilic pneumonia; chronic fatigue syndrome; chronic immune disease associated with organ transplantation; chronic ischemia; chronic liver diseases; chronic mucocutaneous candidiasis; cicatricial pemphigoid; clinically isolated syndrome (CIS) with risk for multiple sclerosis; common varied immunodeficiency (common variable hypogammaglobulinaemia); connective tissue disease associated interstitial lung disease; conjunctivitis; Coombs positive haemolytic anaemia; childhood onset psychiatric disorder; chronic obstructive pulmonary disease (COPD); Crohn's disease; cryptogenic autoimmune hepatitis; cryptogenic fibrosing alveolitis; dacryocystitis; depression; dermatitis scleroderma; dermatomyositis; dermatomyositis/polymyositis associated lung disease; diabetic retinopathy; diabetes mellitus; dilated cardiomyopathy; discoid lupus erythematosus; disk herniation; disk prolapse; disseminated intravascular coagulation; drug-induced hepatitis; drug-induced interstitial lung disease; drug induced immune hemolytic anemia; endocarditis; endometriosis; endophthalmitis; enteropathic synovitis; episcleritis; erythema multiforme; erythema multiforme major; female infertility; fibrosis; fibrotic lung disease; gestational pemphigoid; giant cell arteritis (GCA); glomerulonephritides; goitrous autoimmune hypothyroidism (Hashimoto's disease); Goodpasture's syndrome; gouty arthritis; graft versus host disease (GVHD); Grave's disease; group B streptococci (BGS) infection; Guillain-Barré syndrome (BGS); haemosiderosis associated lung disease; hay fever; heart failure; hemolytic anemia; Henoch-Schoenlein purpura; hepatitis B; hepatitis C; Hughes syndrome; Huntington's chorea; hyperthyroidism; hypoparathyroidism; idiopathic leucopaenia; idiopathic thrombocytopaenia; idiopathic Parkinson's disease; idiopathic interstitial pneumonia; idiosyncratic liver disease; IgE-mediated allergy; immune hemolytic anemia; inclusion body myositis; infectious diseases; infectious ocular inflammatory disease; inflammatory bowel disease; inflammatory demyelinating disease; inflammatory heart disease; inflammatory kidney disease; insulin dependent diabetes mellitus; interstitial pneumonitis; IPF/UIP; iritis; juvenile chronic arthritis; juvenile pernicious anaemia; juvenile rheumatoid arthritis (JRA); Kawasaki's disease; keratitis; keratojunctivitis sicca; Kussmaul disease or Kussmaul-Meier disease; Landry's paralysis; Langerhan's cell histiocytosis; linear IgA disease; livedo reticularis; Lyme arthritis; lymphocytic infiltrative lung disease; macular degeneration; male infertility idiopathic or NOS; malignancies; microscopic vasculitis of the kidneys; microscopic polyangiitis; mixed connective tissue disease associated lung disease; Morbus Bechterev; motor neuron disorders; mucous membrane pemphigoid; multiple sclerosis (all subtypes: primary progressive, secondary progressive, relapsing remitting etc.); multiple organ failure; myalgic encephalitis/royal free disease; myasthenia gravis; myelodysplastic syndrome; myocardial infarction; myocarditis; nephrotic syndrome; nerve root disorders; neuropathy; non-alcoholic steatohepatitis; non A non B hepatitis; optic neuritis; organ transplant rejection; osteoarthritis; osteolysis; ovarian cancer; ovarian failure; pancreatitis; parasitic diseases; Parkinson's disease; pauciarticular JRA; pemphigoid; pemphigus foliaceus; pemphigus vulgaris; peripheral artery occlusive disease (PAOD); peripheral vascular disease (PVD); peripheral artery disease (PAD); phacogenic uveitis; phlebitis; polyarteritis nodosa (or periarteritis nodosa); polychondritis; polymyalgia rheumatica; poliosis; polyarticular JRA; polyendocrine deficiency syndrome; polymyositis; polyglandular deficiency type I and polyglandular deficiency type II; polymyalgia rheumatica (PMR); postinfectious interstitial lung disease; post-inflammatory interstitial lung disease; post-pump syndrome; premature ovarian failure; primary biliary cirrhosis; primary myxoedema; primary Parkinsonism; primary sclerosing cholangitis; primary sclerosing hepatitis; primary vasculitis; prostate and rectal cancer and hematopoietic malignancies (leukemia and lymphoma); prostatitis; psoriasis; psoriasis type 1; psoriasis type 2; psoriatic arthritis; psoriatic arthropathy; pulmonary hypertension secondary to connective tissue disease; pulmonary manifestation of polyarteritis nodosa; pure red cell aplasia; primary adrenal insufficiency; radiation fibrosis; reactive arthritis; Reiter's disease; recurrent neuromyelitis optica; renal disease NOS; restenosis; rheumatoid arthritis; rheumatoid arthritis associated interstitial lung disease; rheumatic heart disease; SAPHO (synovitis, acne, pustulosis, hyperostosis, and osteitis); sarcoidosis; schizophrenia; Schmidt's syndrome; scleroderma; secondary amyloidosis; shock lung; scleritis; sciatica; secondary adrenal insufficiency; sepsis syndrome; septic arthritis; septic shock; seronegative arthropathy; silicone associated connective tissue disease; Sjögren's disease associated lung disease; Sjörgren's syndrome; Sneddon-Wilkinson dermatosis; sperm autoimmunity; spondyloarthropathy; spondylitis ankylosans; Stevens-Johnson syndrome (SJS); Still's disease; stroke; sympathetic ophthalmia; systemic inflammatory response syndrome; systemic lupus erythematosus; systemic lupus erythematosus associated lung disease; systemic sclerosis; systemic sclerosis associated interstitial lung disease; Takayasu's disease/arteritis; temporal arteritis; Th2 Type and Th1 Type mediated diseases; thyroiditis; toxic shock syndrome; toxoplasmic retinitis; toxic epidermal necrolysis; transverse myelitis; TRAPS (Tumor-necrosis factor receptor type 1 (TNFR)-Associated Periodic Syndrome); type B insulin resistance with acanthosis nigricans; type 1 allergic reaction; type-1 autoimmune hepatitis (classical autoimmune or lupoid hepatitis); type-2 autoimmune hepatitis (anti-LKM antibody hepatitis); type II diabetes; ulcerative colitic arthropathy; ulcerative colitis; urticaria; usual interstitial pneumonia (UIP); uveitis; vasculitic diffuse lung disease; vasculitis; vernal conjunctivitis; viral retinitis; vitiligo; Vogt-Koyanagi-Harada syndrome (VKH syndrome); Wegener's granulomatosis; wet macular degeneration; wound healing; *yersinia* and *salmonella* associated arthropathy.

In a particular embodiment, the IL-1β binding proteins and antigen-binding portions thereof of the invention are used to treat rheumatoid arthritis, osteoarthritis, Crohn's disease, multiple sclerosis, insulin dependent diabetes mellitus, and psoriasis.

The IL-1β binding proteins and antigen binding portions thereof of the invention can also be used to treat humans suffering from autoimmune diseases, in particular those associated with inflammation, including ankylosing spondylitis, allergy, autoimmune diabetes, and autoimmune uveitis.

An IL-1β binding protein, or antigen binding portion thereof, of the invention also can be administered with one or more additional therapeutic agents useful in the treatment of autoimmune and inflammatory diseases.

IL-1β binding proteins of the invention, or antigen binding portions thereof, can be used alone or in combination to treat such diseases. It should be understood that the binding proteins of the invention or antigen binding portions thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition, e.g., an agent that affects the viscosity of the composition.

The combinations of the invention include the IL-1β binding proteins, or antigen binding fragments thereof, described herein and at least one additional agent listed below. The combination can also include more than one additional agent, e.g., two or three additional agents if the combination is such that the formed composition can perform its intended function.

Exemplary combinations include the IL-1β binding proteins, or antigen binding fragments thereof, described herein and a non-steroidal anti-inflammatory drug(s) (NSAIDS), such as, for example, ibuprofen. Other exemplary combinations comprise the antibodies, or antigen binding fragments thereof, described herein and corticosteroids including prednisolone. The side-effects of steroid use can be reduced or eliminated by tapering the steroid dose required when treating patients in combination with the anti-IL-1β binding proteins of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-1α, IL-2, IL-3, IL-4, IL-5, IL-6, IL-7, IL-8, IL-15, IL-16, IL-18, IL-21, interferons, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L). Exemplary therapeutic agents for combining with the IL-1a binding proteins, or antigen binding fragments thereof, of the invention interfere at different points in the autoimmune and subsequent inflammatory cascade, for example, TNF antagonists like chimeric, humanized or human TNF antibodies, D2E7, (PCT Publication No. WO 97/29131), CA2 (REMICADEâ), CDP 571, and soluble p55 or p75 TNF receptors, derivatives thereof, (p75TNFR1gG (ENBRELâ) or p55TNFR1gG (Lenercept), and also TNFa converting enzyme (TACE) inhibitors, and other IL-1 inhibitors (Interleukin-1-converting enzyme inhibitors, IL-1RA etc.). Other agents for combining with the antibodies and antigen binding fragments thereof include Interleukin 11, agents that act parallel to, dependent on, or in concert with IL-1a function such as, for example, IL-18 antagonists (e.g., IL-18 binding proteins such as, for example, antibodies or soluble IL-18 receptors, or antigen binding fragments thereof. Additional agents for combining with the antibodies and antigen binding fragments thereof include non-depleting anti-CD4 inhibitors, antagonists of the co-stimulatory pathway CD80 (B7.1) or CD86 (B7.2) including antibodies, soluble receptors, antagonistic ligands, or antigen binding fragments thereof.

The binding proteins of the invention, or antigen binding portions thereof, may also be combined with agents for treatment of rheumatoid arthritis, for example, such as methotrexate, 6-MP, azathioprine sulphasalazine, mesalazine, olsalazine chloroquinine/hydroxychloroquine, pencillamine, aurothiomalate (intramuscular and oral), azathioprine, colchicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents that interfere with signaling by proinflammatory cytokines such as TNFα or IL-1 (e.g., IRAK, NIK, IKK, p38 and MAP kinase inhibitors), IL-1β converting enzyme inhibitors, TNFα, converting enzyme (TACE) inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (ENBREL™ and p55TNFRIgG (Lenercept)), sIL-1RI, sIL-1RII, sIL-6R), antiinflammatory cytokines (e.g., IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, and Mesopram.

Non-limiting examples of therapeutic agents for inflammatory bowel disease with which an IL-1β binding protein (e.g., an antibody), or antigen binding portion thereof, of the invention can be combined include the following: budenoside; epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies to or antagonists of other human cytokines or growth factors, for example, TNF, LT, IL-1β, IL-2, IL-6, IL-7, IL-8, IL-15, IL-16, IL-17, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD90 and their ligands. The binding proteins of the invention, or antigen binding portions thereof, may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1β converting enzyme inhibitors, TNFα converting enzyme inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R) and antiinflammatory cytokines (e.g., IL-4, IL-10, IL-11, IL-13, and TGFβ).

Exemplary examples of therapeutic agents for Crohn's disease in which an IL-1β binding protein or an antigen binding portion thereof, as described herein, can be combined include the following: TNF antagonists, for example, anti-TNF antibodies, D2 E7 (PCT Publication No. WO 97/29131; HUMIRA®), CA2 (REMICADE®), CDP 571, TNFR-Ig constructs, (p75TNFRIgG (ENBREL®) and p55TNFRIgG (Lenercept)) inhibitors and PDE4 inhibitors. Binding proteins of the invention, or antigen binding portions thereof, can be combined with corticosteroids, for example, budenoside and dexamethasone. Binding proteins of the invention, or antigen binding portions thereof, may also be combined with agents such as sulfasalazine, 5-aminosalicylic acid and olsalazine, and agents that interfere with synthesis or action of proinflammatory cytokines such as IL-1, for example, IL-1β converting enzyme inhibitors and IL-1RA. Binding proteins of the invention or antigen binding portion thereof may also be used with T cell signaling inhibitors, for example, tyrosine kinase inhibitors 6-mercaptopurines. Binding proteins of the invention, or antigen binding portions thereof, can be combined with IL-11. Binding proteins of the invention, or antigen binding portions thereof, can be combined with mesalamine, prednisone, azathioprine, mercaptopurine, infliximab, methylprednisolone sodium succinate, diphenoxylate/atrop sulfate, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, methylprednisolone, natalizumab and interferon-gamma.

Non-limiting examples of therapeutic agents for multiple sclerosis with which an IL-1β binding protein, or antigen binding portion, of the invention can be combined include the following: corticosteroids, prednisolone, methylprednisolone, azathioprine, cyclophosphamide, cyclosporine, methotrexate, 4-aminopyridine, tizanidine, interferon-β1a (AVONEX®; Biogen), interferon-β1b (BETASERON®; Chiron/Berlex), interferon α-n3 (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.), hyperbaric oxygen, intravenous immunoglobulin, clabribine, antibodies to or antagonists or inhibitors of other human cytokines or growth factors and their receptors, for example, TNF, LT, IL-1β, IL-2, IL-6, IL-7, IL-8, IL-1A, 1L-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD19, CD20, CD25, CD28, CD30, CD40, CD45, CD69, CD80, CD86, CD90 or their ligands. The antibodies of the invention, or antigen binding portions thereof, may also be combined with agents, such as FK506, rapamycin, mycophenolate mofetil, leflunomide, NSAIDs, for example, ibuprofen, phosphodiesterase inhibitors, adensosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1b converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R), antiinflammatory cytokines (e.g., IL-4, IL-10, IL-13 and TGFβ), COPAXONE®, and caspase inhibitors, for example inhibitors of caspase-1.

The IL-1β binding proteins of the invention, or antigen binding portions thereof, may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-β2, tiplimotide, VLA-4 antagonists (for example, TR-14035, VLA4 Ultrahaler, Antegran-ELAN/Biogen), interferon gamma antagonists, IL-4 agonists.

Non-limiting examples of therapeutic agents for the treatment or prevention of angina with which an IL-1β binding protein, or antigen binding portion thereof, of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil hcl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril, and bisoprolol fumarate.

Non-limiting examples of therapeutic agents for the treatment or prevention of ankylosing spondylitis with which a binding protein, or antigen binding portion thereof, of the invention can be combined include the following: ibuprofen, diclofenac and misoprostol, naproxen, meloxicam, indomethacin, diclofenac, celecoxib, rofecoxib, sulfasalazine, methotrexate, azathioprine, minocyclin, prednisone, etanercept, and infliximab.

Non-limiting examples of therapeutic agents for the treatment or prevention of asthma with which an IL-1β binding protein, or antigen binding portion thereof, of the invention can be combined include the following: albuterol, salmeterol/fluticasone, montelukast sodium, fluticasone propionate, budesonide, prednisone, salmeterol xinafoate, levalbuterol hcl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin hcl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine hcl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, and metaproterenol sulfate.

Non-limiting examples of therapeutic agents for the treatment or prevention of COPD with which an IL-1β binding protein, or antigen binding portion thereof, of the invention can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol hcl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast, and roflumilast.

Non-limiting examples of therapeutic agents for the treatment or prevention of HCV with which an IL-1β binding protein, or antigen binding portion thereof, of the invention can be combined include the following: interferon-alpha-2a, interferon-alpha-2b, interferon-alpha con1, interferon-alpha-n1, pegylated interferon-alpha-2a, pegylated interferon-alpha-2b, ribavirin, peginterferon alfa-2b +ribavirin, ursodeoxycholic acid, glycyrrhizic acid, thymalfasin, maxamine, VX-497 and any compounds that are used to treat HCV through intervention with the following targets: HCV polymerase, HCV protease, HCV helicase, HCV IRES (internal ribosome entry site).

Non-limiting examples of therapeutic agents for the treatment or prevention of idiopathic pulmonary fibrosis with which a binding protein, or antigen binding portion thereof, of the invention can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil, and interferon-gamma-1b.

Non-limiting examples of therapeutic agents for the treatment or prevention of myocardial infarction with which an IL-1β binding protein, or antigen binding portion thereof, of the invention can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hcl/mag carb, bumetanide, alteplase, enalaprilat, amiodarone hydrochloride, tirofiban hcl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine hcl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for the treatment or prevention of psoriasis with which an IL-1β binding protein, or antigen binding portion thereof, of the invention can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, and sulfasalazine.

Non-limiting examples of therapeutic agents for the treatment or prevention of psoriatic arthritis with which an IL-1β binding protein, or antigen binding portion thereof, of the invention can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, and efalizumab.

Non-limiting examples of therapeutic agents for the treatment or prevention of restenosis with which an IL-1β binding protein, or antigen binding portion thereof, of the invention can be combined include the following: sirolimus, paclitaxel, everolimus, tacrolimus, ABT-578, and acetaminophen.

Non-limiting examples of therapeutic agents for the treatment or prevention of sciatica with which an IL-1β binding protein, or antigen binding portion thereof, of the invention can be combined include the following: hydrocodone bitartrate/apap, rofecoxib, cyclobenzaprine hcl, methylprednisolone, naproxen, ibuprofen, oxycodone hcl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone hcl, tizanidine hcl, diclofenac sodium/misoprostol, propoxyphene napsylate/apap, asa/oxycod/oxycodone ter, ibuprofen/hydrocodone bit, tramadol hcl, etodolac, propoxyphene hcl, amitriptyline hcl, carisoprodol/codeine phos/asa, morphine sulfate, multivitamins, naproxen sodium, orphenadrine citrate, and temazepam.

Non-limiting examples of therapeutic agents for the treatment or prevention of systemic lupus erythematosis (SLE) with which an IL-1β binding protein, or an antigen binding portion thereof, of the invention can be combined include the following: NSAIDS, for example, diclofenac, naproxen, ibuprofen, piroxicam, indomethacin, COX2 inhibitors, for example, celecoxib, rofecoxib, valdecoxib, anti-malarials, for example, hydroxychloroquine, steroids, for example, prednisone, prednisolone, budenoside, dexamethasone, cytotoxics, for example, azathioprine, cyclophosphamide, mycophenolate mofetil, methotrexate, inhibitors of PDE4 or of purine synthesis inhibitor, for example, CELLCEPT®. Binding proteins of the invention, or antigen binding portions thereof, may also be combined with agents such as sulfasalazine, 5-aminosalicylic acid, olsalazine, Imuran and agents which interfere with synthesis, production or action of proinflammatory cytokines such as IL-1, for example, caspase inhibitors like IL-1β converting enzyme inhibitors and IL-1ra. Binding proteins of the invention, or antigen binding portion thereof, may also be used with T cell signaling inhibitors, for example, tyrosine kinase inhibitors, or molecules that target T cell activation molecules, for example, CTLA-4-IgG or anti-B7 family antibodies, and anti-PD-1 family antibodies. Binding proteins of the invention, or antigen binding portions thereof, can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. Binding proteins of the invention, or antigen binding portion thereof, may also be used with LJP 394 (abetimus), agents that deplete or inactivate B-cells, for example, rituximab (anti-CD20 antibody), lymphostat-B (anti-BlyS antibody), TNF antagonists, for example, anti-TNF antibodies, D2E7 (PCT Publication No. WO 97/29131; HUMIRA®), CA2 (REMICADE®), CDP 571, TNFR-Ig constructs, (p75TNFRIgG (ENBREL®) and p55TNFRIgG (Lenercept)).

The pharmaceutical compositions of the invention may include a "therapeutically effective amount" or a "prophylactically effective amount" of an IL-1β binding protein, or antigen binding portion thereof, of the invention. A "therapeutically effective amount" refers to an amount effective, at dosages and for periods of time necessary, to achieve the desired therapeutic result. A therapeutically effective amount of a binding protein, or antigen binding portion thereof, described herein may be determined by a person skilled in the art and may vary according to factors such as the disease state, age, sex, and weight of the individual, and the ability of the antibody, or antigen binding portion thereof, to elicit a desired response in the individual. A therapeutically effective amount is also one in which any toxic or detrimental effects of the antibody, or antigen binding portion thereof, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of IL-1β binding protein, or antigen binding portion thereof, of the invention is about 0.1 to about 20 mg/kg, about 1 to about 10 mg/kg. Dosage values may vary with the type and severity of the condition to be alleviated. For any particular subject, specific dosage regimens should be adjusted over time according to the individual need and the professional judgment of the person administering or supervising the administration of the compositions. Dosage ranges set forth herein are exemplary only and are not intended to limit the scope or practice of the claimed composition.

It will be readily apparent to those skilled in the art that other suitable modifications and adaptations of the compositions and the methods of the invention described herein are obvious and may be made using suitable equivalents without departing from the scope of the invention or the embodiments disclosed herein. The present invention will be more clearly understood by reference to the following examples, which are included for purposes of illustration only and are not intended to be limiting of the invention.

EXAMPLES

Example 1

Generation Of Anti-Human IL-1β Monoclonal Antibodies

Mouse anti-human IL-1β monoclonal antibodies are obtained as follows:

Example 1.1

Immunization Of Mice With Human IL-1β Antigen

Twenty micrograms of recombinant purified human IL-1β (R&D Systems, Minneapolis, Minn., USA) mixed with complete Freund's adjuvant or Immunoeasy adjuvant (Qiagen, Valencia, Calif.) is injected subcutaneously into five 6-8 week-old Balb/C, five C57B/6 mice, and five AJ mice on Day 1. On days 24, 38, and 49, twenty micrograms of recombinant purified human IL-1β variant mixed with incomplete Freund's adjuvant or Immunoeasy adjuvant is injected subcutaneously into the same mice. On day 84 or day 112 or day 144, mice are injected intravenously with 1 µg recombinant purified human IL-1β variant.

Example 1.2

Generation of Hybridoma

Splenocytes obtained from the immunized mice described in Example 1.1 are fused with SP2/O-Ag-14 cells at a ratio of 5:1 according to the established method described in Kohler, G. and Milstein (1975) Nature 256:495 to generate hybridomas. Fusion products are plated in selection media containing azaserine and hypoxanthine in 96-well plates at a density of $2.5 \times 10^6$ spleen cells per well. Seven to ten days post fusion, macroscopic hybridoma colonies are observed. Supernatant from each well containing hybridoma colonies is tested by ELISA for the presence of antibody to IL-1β (as described in Example 3.1). Supernatants displaying IL-1β specific activity are then tested for the ability to neutralize IL-1β in the MRC-5 bioassay for IL-8 (as described in Example 3.2).

Example 1.3

Identification And Characterization Of Anti Human IL-1β Monoclonal Antibodies

Hybridomas producing antibodies that bound IL-1β and are capable of binding IL-1β specifically and particularly those with $IC_{50}$ values in the MRC-5 bioassay of 5 nM or less than 5 nM are scaled up and cloned by limiting dilution.

Hybridoma cells are expanded into media containing 10% low IgG fetal bovine serum (Hyclone #SH30151, Logan, Utah). On average, 250 mL of each hybridoma supernatant (derived from a clonal population) is harvested, concentrated and purified by protein A affinity chromatography by standard methods. The ability of purified mAbs to inhibit IL-1β activity is determined using the MRC-5 bioassay as described in Example 3.2.

Example 1.4

Determination Of The Amino Acid Sequence Of The Variable Region For Each Murine Anti-Human IL-1β Monoclonal Antibody For each amino acid sequence determination, approximately $10 \times 10^6$ hybridoma cells are isolated by centrifugation and processed to isolate total RNA with Trizol (Gibco BRL/Invitrogen, Carlsbad, Calif.) following manufacturer's instructions. Total RNA is subjected to first strand DNA synthesis using the SuperScript First-Strand Synthesis System (Invitrogen, Carlsbad, Calif.) per the manufacturer's instructions. Oligo(dT) is used to prime first-strand synthesis to select for poly(A)$^+$ RNA. The first-strand cDNA product is then amplified by PCR with primers designed for amplification of murine immunoglobulin variable regions (Ig-Primer Sets, Novagen, Madison, Wis.). PCR products are resolved on an agarose gel, excised, purified, and then subcloned with the TOPO Cloning kit into pCR2.1-TOPO vector (Invitrogen, Carlsbad, Calif.) and transformed into TOP10 chemically competent *E. coli* (Invitrogen, Carlsbad, Calif.). Colony PCR is performed on the transformants to identify clones containing insert. Plasmid DNA is isolated from clones containing insert using a QIAprep Miniprep kit (Qiagen, Valencia, Calif.). Inserts in the plasmids are sequenced on both strands to determine the variable heavy or variable light chain DNA sequences using M13 forward and M13 reverse primers (Fermentas Life Sciences, Hanover Md.). Variable heavy and variable light chain sequences of the anti-IL-1β monoclonal antibodies are shown in Table 5.

Example 2

Recombinant Anti-Human IL-1β Antibodies

Example 2.1

Construction And Expression Of Recombinant Chimeric Anti-Human IL-1β Antibodies

The DNA encoding the heavy chain constant region of murine anti-human IL-1βmonoclonal antibody 1B12.4H4 was replaced by a cDNA fragment encoding the human IgG1 constant region containing 2 hinge-region amino acid mutations by homologous recombination in bacteria. These mutations are a leucine to alanine change at position 234 (EU numbering) and a leucine to alanine change at position 235 (Lund et al. (1991) J. Immunol. 147:2657). The light chain constant region of each of these antibodies was replaced by a human kappa constant region.

Full-length chimeric antibodies were transiently expressed in HEK 293-6E cells by co-transfection of chimeric heavy and light chain cDNAs ligated into the pHybE expression plasmid (US Patent Publication No. US 20090239259). Cell supernatants containing recombinant chimeric antibody were purified by Protein A Sepharose chromatography and bound antibody was eluted by addition of acid buffer. Antibodies were neutralized and dialyzed into PBS.

The heavy chain cDNA encoding chimeric 1B12.4H4 was co-transfected with the 1B12.4H4 chimeric light chain cDNA (both ligated in the pHybE vector) into HEK 293-6E cells. Cell supernatant containing recombinant chimeric antibody was purified by Protein A Sepharose chromatography and bound antibody was eluted by addition of acid buffer. Antibodies were neutralized and dialyzed into PBS. The purified chimeric anti-human IL-1β monoclonal antibodies were then tested for their ability to inhibit the IL-1β induced production of IL-8 by MRC-5 cells as described in Example 3.2.

Example 2.2

Construction And Expression Of Humanized Anti-Human IL-1β Antibodies

Example 2.2.1

Selection Of Human Antibody Frameworks

The canonical structures of the VH and VL CDRs were determined according to the method of Huang et al. (2005) Methods 36:35-42. Based on the canonical structures, the appropriate acceptor human VH framework sequences were 3-13, 3-53, 3-66, 4-34, and 4-59 and the appropriate acceptor human VL framework sequences included Vk1, some Vk3, Vk5, and Vk6 subgroups. hJH4 was selected as the acceptor human FR4 sequence based on an alignment of amino acids 109-122 of the 1B12VH region with hJH1-6 sequences.

Four additional VH sequences (1B12VHx, -xx, -xxx, and -xxxx) were created by gradually replacing CDR or framework residues with 'X'. 1B12VHs was the VH sequence with D and J regions removed. The five sequences were aligned with human VH sequences in the Align X program of Vector NTI® software (Invitrogen, Carlsbad, Calif.). Focusing on overall framework or only specific residues important for loop conformation and VH/VL interface, the VH4-59 had the best overall homology to the 1B12 VH sequence. This framework was selected as the accepter human germline framework for grafting 1B12 VH CDR sequences. The VH3-53 was selected as the alternative acceptor human framework from a different VH family. VH4 sequences were aligned to identify framework residues in VH4-59 that could be changed into VH4 consensus sequence to minimize immunogenicity potential of the humanized sequence. Sequence alignment of VH4-59 showed there was no need to introduce framework residue changes to bring VH4-59 to a VH4 consensus sequence. Sequence alignment showed that the VH4-59 sequence to be used as an acceptor framework was the dominant consensus. Similarly, all VH3 sequences were aligned to identify framework residues in VH3-53 that could be changed into VH3 consensus sequence to minimize immunogenicity potential. Two VH3 consensus changes (I12V and V29F) were identified. The alignment also showed that the VH3-53 sequence to be used as an acceptor framework was the first sequence from the three known VH3-53 polymorphisms. Sequences in set one having from one to eight out of the nine proposed back-mutations in any combinations with or without the Q1E change can be made to produce additional humanized 1B12 VH sequences with less immunogenicity potential or better overall identity to naturally occurring human VH sequences from the VH4-59 germline sequence.

To determine the prevalence of the proposed back-mutations in human antibodies originated from VH4-59, human VH sequences derived from VH4-59 were downloaded from the NCBI IgBlast database into a batch fasta file, aligned by ClustalW, and visualized by logobar. The output.eps file was edited by Adobe Illustrator to remove gaps, signal peptide, most of CDR3, and constant region sequences. This analysis was useful for understanding whether the proposed back-mutations and the mouse VH CDR residues were represented in 825 natural human antibodies that could be originated from VH4-59. Of the nine proposed (G27F, I29L, I48L, V67L, V71K, T73N, N76S, F78V, and R94K) back-mutations, G27F, I29L, V67L, N76S, F78V, and R94K were observed in more than 1% of these sequences.

Sequences in set two having from one to nine out of the ten proposed back-mutations in any combinations having zero to two out of the two I12V and V29F VH3 framework consensus changes can be made to produce additional humanized 1B12 VH sequences with less immunogenicity potential or better overall identity to naturally occurring human VH sequences from the VH3-53 germline sequence. Human VH sequences derived from VH3-53 were downloaded from the NCBI IgBlast database into a batch fasta file, aligned by ClustalW, and visualized by logobar. The output.eps file was edited by Adobe Illustrator to remove gaps, signal peptide, and constant region sequences. This analysis was useful for understanding whether the proposed ten back-mutations and the mouse VH CDR residues were represented in 174 natural human antibodies that could be originated from VH3-53. Of the ten proposed (A24V, F29L, V37I, V48L, S49G, F67L, R71K, N76S, L78V, and R94K) back-mutations, A24V, F29L, R71K, N76S, L78V, and R94K were observed in more than 1% of these sequences.

Residues supporting loop structures and VH/VL interface in VL sequences were summarized in PCT Publication No. WO2008021156. Four additional VL sequences (1B12VLx, -xx, -xxx, and -xxxx) were created by gradually replacing CDR or framework residues with 'X'. 1B12VLs is the VL sequence with J region removed. The five sequences were aligned with human Vk sequences in the Align X program of Vector NTI® software. Only human Vk germline sequences having 2-1-1 canonical CDR structures were considered. The human Vk germline 1-33/O18 was selected as the acceptor framework for 1B12.4H4 VL humanization. The human Vk germline 6D41/A14 was selected as the back-up acceptor framework for humanization from a different subgroup. All human Vk1 germline sequences were aligned to identify potential framework residues in 1-33/O18 that should be changed into Vk1 consensus to minimize immunogenicity potential. Two Vk1 consensus changes (F73L and I83F) were identified. These changes minimized the immunogenicity potential of the humanized 1B12 VL sequence. The same analysis was not done for the 6D41/A14 as there were only two different germline sequences in the Vk6 subgroup.

Additional sequences of set one containing one to six out of the seven proposed back-mutations (I2T, M4V, A43P, Y49S, G64S, D1E, and Q3T) in any combinations with or without the I83F Vk1 consensus change can be made to achieve better IgG function, less immunogenicity potential, or better overall identity to naturally occurring human VL sequences from the O18 germline sequence. Additional sequences of set two having one to six out of the seven proposed back-mutations (V2T, M4V, A43P, K49S, G64S, D1E, and V3T) in any combinations can be made to achieve better IgG function, less immunogenicity potential, or better overall homology to naturally occurring human VL sequences from the 6D41/A14 germline sequence.

Human Vk sequences derived from 1-33/O18 were downloaded from the NCBI IgBlast database into one batch fasta file, aligned by ClustalW, and visualized by logobar. The output.eps file was edited by Adobe Illustrator to remove gaps, signal peptide, and constant region sequences. This analysis was useful for understanding whether the proposed back-mutations and the mouse VH CDR residues were represented in 260 natural human antibodies that could be originated from 1-33/O18. Of the seven proposed back-mutations, D1E and Y49S were observed in more than 1% of these sequences.

Example 2.2.2

Humanization Of Anti-Human IL-1β Monoclonal Antibody 1B12.4H4

The heavy chain CDR sequences from the anti-IL-1β antibody 1B12.4H4 described in Table 5 were grafted in silico onto two human frameworks. The first set comprises the mAbs h1B12VH.1z, h1B12VH.1, and h1B12VH.1a. h1B12VH.1z is a CDR-grafted humanized 1B12 VH containing VH4-59 and JH4 framework sequences. h1B12VH.1 is a humanized design further incorporating a Q1E framework change to prevent N-terminal pyroglutamate formation. h1B12VH.1a is a humanized design containing the Q1E change and all possible framework back-mutations G27F, I29L, I48L, V67L, V71K, T73N, N76S, F78V, and R94K.

The second set comprises the mAbs h1B12VH.2z, h1B12VH.2, and h1B12VH.2a. h1B12VH.2z is a CDR-grafted humanized 1B12 VH containing VH3-53 and hJH4 framework sequences. h1B12VH.2 is a humanized design incorporating I12V and V29F VH3 framework consensus changes. h1B12VH.2a is a humanized design containing the VH3 framework consensus changes and all possible framework back-mutations A24V, F29L (F is a VH3 consensus sequence), V37I, V48L, S49G, F67L, R71K, N76S, L78V, and R94K. No N-linked glycosylation pattern (N-{P}-S/T) was found in these proposed constructs. Not all back-mutations may be needed. The back-mutations I48L, V71K, and T73N in set 1 and F29L, V37I, V48L, S49G, and F67L in set 2 are not represented in human antibodies. Some back-mutations could be removed during subsequent affinity maturation process if so desired.

The light chain CDR sequences from the anti-IL-1β antibody 1B12.4H4 described in Table 5 were grafted in silico onto two human frameworks. The first set comprises the mAbs h1B12VL.1z, h1B12VL.1, h1B12VL.1a, and h1B12VL.1b. h1B12VL.1z is a direct CDR-grafted humanized 1B12 VL containing O18 and Jk2 framework sequences. h1B12VL.1 is a humanized design incorporating I83F Vk1 framework consensus change. h1B12VL.1a is a humanized design containing the consensus change and 5 framework back-mutations (I2T, M4V, A43P, Y49S, G64S). h1B12VL.1b is a humanized design containing the consensus changes and 7 framework back-mutations (5 above and 2 additional N-terminal back-mutations D1E and Q3T). The second set comprises the mAbs h1B12VL.2, h1B12VL.2a, and h1B12VL.2b. h1B12VL.2 is a direct CDR-grafted humanized 1B12 VL containing A14 and Jk2 framework sequences. h1B12VL.2a is a humanized design containing 5 framework back-mutation (V2T, M4V, A43P, K49S, G64S). h1B12VL.2b is a humanized design containing 7 framework back-mutations (5 above and 2 additional N-terminal back-mutations D1E and V3T). No N-linked glycosylation pattern (N-{P}-S/T) was found in the proposed constructs. Not all back-mutations may be needed. The back-mutations I2T, Q3T, M4V, A43P, and G64S in version 1 are not represented in human antibodies. There are very few human antibodies originated from 6D41/A14 germline sequence. Some back-mutations could be removed during subsequent affinity maturation process if so desired.

Table 6 is a list of amino acid sequences of VH and VL regions of humanized anti-hIL-1β antibodies of the invention.

TABLE 6

List Of Amino Acid Sequences Of Humanized 1B12 VH/VL Variants

| SEQ ID No. | Protein region | Sequence 12345678901234567890123456789 |
|---|---|---|
| 28 | h1B12.4H4VH.1z | QVQLQESGPGLVKPSETLSLTCTVSGGSIS DYGVSWIRQPPGKGLEWIGLIWGGGDTYYN SPLKSRVTISVDTSKNQFSLKLSSVTAADT AVYYCARQRTLWGYDLYGMDYWGQGTLVTV SS |
| 29 | h1B12.4H4VH.1 | EVQLQESGPGLVKPSETLSLTCTVSGGSIS DYGVSWIRQPPCKGLEWIGLIWGGGDTYYN SPLKSRVTISVDTSKNQFSLKLSSVTAADT AVYYCARQRTLWGYDLYGMDYWGQGTLVTV SS |
| 30 | h1B12.4H4VH.1a | EVQLQESGPGLVKPSETLSLTCTVSGFSLS DYGVSWIRQPPGKGLEWLGLIWGGGDTYYN SPLKSRLTISKDNSKSQVSLKLSSVTAADT AVYYCAKQRTLWGYDLYGMDYWGQGTLVTV SS |
| 31 | h1B12.4H4VH.2z | EVQLVESGGGLIQPGGSLRLSCAASGFTVS DYGVSWVRQAPGKGLEWVSLIWGGGDTYYN SPLKSRFTISRDNSKNTLYLQMNSLRAEDT AVYYCARQRTLWGYDDYGMDYWGQGTLVTV SS |
| 32 | h1B12.4H4VH.2 | EVQLVESGGGLVQPGGSLRLSCAASGFTFS DYGVSWVRQAPGKGLEWVSLIWGGGDTYYN SPLKSRFTISRDNSKNTLYLQMNSLRAEDT AVYYCARQRTLWGYDLYGMDYWGQGTLVTV SS |
| 33 | h1B12.4H4VH.2a | EVQLVESGGGLVQPGGSLRLSCAVSGFTLS DYGVSWIRQAPGKGLEWLGLIWGGGDTYYN SPLKSRLTISKDNSKSTVYLQMNSLRAEDT AVYYCAKQRTLWGYDLYGMDYWGQGTLVTV SS |
| 34 | h1B12.4H4VL.1 | DIQMTQSPSSLSASVGDRVTITCITSTDID VDMNWYQQKEGKAEKLLIYQGNTLRPGVPS RFSGSGSGTDFTFTISSLQPEDFATYYCLQ SDNLPLTFGQGTKLEIK |
| 35 | h1B12.4H4VL.1z | DIQMTQSPSSLSASVGDKVTITCITSTDID VDMNWYQQKPGKAPKLLIYQGNTLRPGVPS RFSGSGSGTDFTFTISSLQPEDIATYYCLQ SDNLPLTFGQGTKLEIK |
| 36 | h1B12.4H4VL.1a | DTQVTQSPSSLSASVGDRVTITCITSTDID VDMNWYQQKPGKPPKLLISQGNTLRPGVPS RFSSSGSGTDFTFTISSLQPEDFATYYCLQ SDNLPLTFGQGTKLEIK |
| 37 | h1B12.4H4VL.1b | ETTVTQSPSSLSASVGDRVTITCITSTDID VDMNWYQQKPGKPPKLLISQGNTLRPGVPS RFSSSGSGTDFTFTISSLQPEDFATYYCLQ SDNLPLTFGQGTKLEIK |
| 38 | h1B12.4H4VL.2 | DVVMTQSPAFLSVTPGEKVTITCITSTDID VDMNWYQQKPDQAPKLLIKQGNTLRPGVPS RFSGSGSGTDFTFTISSLEAEDAATYYCLQ SDNLPLTFGQGTKLEIK |
| 39 | h1B12.4H4VL.2a | DTVVTQSPAFLSVTPGEKVTITCITSTDID VDMNWYQQKPDQPPKLLISQGNTLRPGVPS RFSSSGSGTDFTFTISSLEAEDAATYYCLQ SDNLPLTFGQGTKLEIK |

TABLE 6-continued

List Of Amino Acid Sequences Of Humanized 1B12 VH/VL Variants

| SEQ ID No. | Protein region | Sequence<br>123456789012345678901234567890 |
|---|---|---|
| 40 | h1B12.4H4VL.2b | ETTVTQSPAFLSVTPGEKVTITCITSTDID<br>VDMNWYQQKPDQPPKLLISQGNTLRPGVPS<br>RFSSSGSGTDFTFTISSLEAEDAATYYCLQ<br>SDNLPLTFGQGTKLEIK |

Example 2.2.3

Construction Of Humanized Antibodies

The sequences can be used to synthesize nucleic acids using standard DNA synthesis or amplification technologies and assembling the desired antibody fragments into expression vectors, using standard recombinant DNA technology, for expression in cells. For example, nucleic acid codons are determined from amino acids sequences and oligonucleotide DNA is synthesized by Blue Heron Biotechnology, Inc. (www. blueheronbio.com) Bothell, Wash. USA. The oligonucleotides are assembled into 300-2,000 base pair double-stranded DNA fragments, cloned into a plasmid vector and sequence-verified. Cloned fragments are assembled using an enzymatic process to yield the complete gene and subcloned into an expression vector. (See U.S. Pat. Nos. 7,306,914; 7,297,541; 7,279,159; 7,150,969; 20080115243; 20080102475; 20080081379; 20080075690; 20080063780; 20080050506; 20080038777; 20080022422; 20070289033; 20070287170; 20070254338; 20070243194; 20070225227; 20070207171; 20070150976; 20070135620; 20070128190; 20070104722; 20070092484; 20070037196; 20070028321; 20060172404; 20060162026; 20060153791; 20030215458; and 20030157643).

For example, in silico constructed humanized antibodies described above can be inserted into the multiple cloning site in a pHybE vector (US Patent Publication No. US 2009/0239259). Bacterial colonies are isolated and plasmid DNA extracted; cDNA inserts are sequenced in their entirety. Correct humanized heavy and light chains corresponding to each antibody are co-transfected into HEK 293-6E cells to transiently produce full-length humanized anti-human IL-1β antibodies. pHybE vectors containing the heavy chain grafted cDNA and the light chain grafted cDNA were co-transfected into HEK 293-6E cells. Cell supernatants containing recombinant chimeric antibody are purified by Protein A Sepharose chromatography and bound antibody is eluted by addition of acid buffer. Antibodies are neutralized and dialyzed into PBS. Humanized antibodies are described in Table 7.

The different combinations of humanized 1B12 antibody based on the VH and VL shuffling are listed in Table 7.

TABLE 7

Combinations Of Humanized 1B12 Antibody Based On The VH And VL Shuffling

| | 1B12VL | h1B12VL.1z | h1B12VL.1 | h1B12VL.1a | h1B12VL.1b | h1B12VL.2 | h1B12VL.2a | h1B12VL.2b |
|---|---|---|---|---|---|---|---|---|
| 1B12VH | | | | | | | | |
| h1B12VH.1z | | | | | | | | |
| h1B12VH.1 | | | | | | | | |
| h1B12VH.1a | | | | 1 | 2 | | 3 | 4 |
| h1B12VH.2z | | | | | | | | |
| h1B12VH.2 | | | | | | | | |
| h1B12VH.2a | | | | 5 | 6 | | 7 | 8 |

Table 8 provides humanized variable regions of the murine monoclonal antibody 1B12 that were cloned into IgG expression vectors for functional characterization. CDRs are shown in bold.

TABLE 8

Humanized Variable Regions Of The Murine Monoclonal Antibody 1B12

| SEQ ID No. | Protein region | | | Sequence<br>123456789012345678901234567890 |
|---|---|---|---|---|
| 30 | 1B12.1<br>VH | | | EVQLQESGPGLVKPSETLSLTCTVSGFSLS<br>DYGVSWIRQPPGKGLEWLGLIWGGGDTYYN<br>SPLKSRLTISKDNSKSQVSLKLSSVTAADT<br>AVYYCAKQRTLWGYDLYGMDYWGQGTLVTV<br>SS |
| 41 | 1B12.1VH | CDR H1 | Residues 31-35 of SEQ ID NO: 26 | DYGVS |
| 42 | 1B12.1VH | CDR H2 | Residues 50-65 of SEQ ID NO: 26 | LIWGGGDTYYNSPLKS |

TABLE 8 -continued

Humanized Variable Regions Of The Murine Monoclonal Antibody 1B12

| SEQ ID No. | Protein | region | | Sequence 12345678901234567890123456789 0 |
|---|---|---|---|---|
| 43 | 1B12.1VH | CDR H3 | Residues 98-111 of SEQ ID NO: 26 | QRTLWGYDLYGMDY |
| 36 | 1B12.1VL | | | DTQVTQSPSSLSASVGDRVTITCITSTDID VDMNWYQQKPGKPPKLLISQGNTLRPGVPS RFSSSGSGTDFTFTISSLQPEDFATYYCLQ SDNLPLTFGQGTKLEIK |
| 44 | 1B12.1VL | CDR L1 | Residues 24-34 of SEQ ID NO: 27 | ITSTDIDVDMN |
| 45 | 1B12.1VL | CDR L2 | Residues 50-56 of SEQ ID NO: 27 | QGNTLRP |
| 46 | 1B12.1VL | CDR L3 | Residues 89-97 of SEQ ID NO: 27 | LQSDNLPLT |
| 30 | 1B12.2VH | | | EVQLQESGPGLVKPSETLSLTCTVSGFSLS DYGVSWIRQPPGKGLEWLGLIWGGGDTYYN SPLKSRLTISKDNSKSQVSLKLSSVTAADT AVYYCAKQRTLWGYDLYGMDYWGQGTLVTV SS |
| 41 | 1B12.2VH | CDR H1 | Residues 31-35 of SEQ ID NO: 26 | DYGVS |
| 42 | 1B12.2VH | CDR H2 | Residues 50-65 of SEQ ID NO: 26 | LIWGGGDTYYNSPLKS |
| 43 | 1B12.2VH | CDR H3 | Residues 98-111 of SEQ ID NO:26 | QRTLWGYDLYGMDY |
| 37 | 1B12.2VL | | | ETTVTQSPSSLSASVGDRVTITCITSTDID VDMNWYQQKPGKPPKLLISQGNTLRPGVPS RFSSSGSGTDFTFTISSLQPEDFATYYCLQ SDNLPLTFGQGTKLEIK |
| 44 | 1B12.2VL | CDR L1 | Residues 24-34 of SEQ ID NO: 27 | ITSTDIDVDMN |
| 45 | 1B12.2VL | CDR L2 | Residues 50-56 of SEQ ID NO: 27 | QGNTLRP |
| 46 | 1B12.2VL | CDR L3 | Residues 89-97 of SEQ ID NO: 27 | LQSDNLPLT |
| 30 | 1B12.3VH | | | EVQLQESGPGLVKPSETLSLTCTVSGFSLS DYGVSWIRQPPGKGLEWLGLIWGGGDTYYN SPLKSRLTISKDNSKSQVSLKLSSVTAADT AVYYCAKQRTLWGYDLYGMDYWGQGTLVTV SS |
| 41 | 1B12.3VH | CDR H1 | Residues 31-35 of SEQ ID NO: 26 | DYGVS |

TABLE 8 -continued

Humanized Variable Regions Of The Murine Monoclonal Antibody 1B12

| SEQ ID No. | Protein region | | | Sequence 12345678901234567890123456789 0 |
|---|---|---|---|---|
| 42 | 1B12.3VH | CDR H2 | Residues 50-65 of SEQ ID NO: 26 | LIWGGGDTYYNSPLKS |
| 43 | 1B12.3VH | CDR H3 | Residues 98-111 of SEQ ID NO: 26 | QRTLWGYDLYGMDY |
| 39 | 1B12.3VL | | | DTVVTQSPAFLSVTPGEKVTITCITSTDID VDMNWYQQKPDQPPKLLISQGNTLRPGVPS RFSSSGSGTDFTFTISSLEAEDAATYYCLQ SDNLPLTFGQGTKLEIK |
| 44 | 1B12.3VL | CDR L1 | Residues 24-34 of SEQ ID NO: 27 | ITSTDIDVDMN |
| 45 | 1B12.3VL | CDR L2 | Residues 50-56 of SEQ ID NO: 27 | QGNTLRP |
| 46 | 1B12.3VL | CDR L3 | Residues 89-97 of SEQ ID NO: 27 | LQSDNLPLT |
| 30 | 1B12.4VH | | | EVQLQESGPGLVKPSETLSLTCTVSGFSLS DYGVSWIRQPPGKGLEWLGLIWGGGDTYYN SPLKSRLTISKDNSKSQVSLKLSSVTAADT AVYYCAKQRTLWGYDLYGMDYWGQGTLVTV SS |
| 41 | 1B12.4VH | CDR H1 | Residues 31-35 of SEQ ID NO: 26 | DYGVS |
| 42 | 1B12.4VH | CDR H2 | Residues 50-65 of SEQ ID NO: 26 | LIWGGGDTYYNSPLKS |
| 43 | 1B12.4VH | CDR H3 | Residues 98-111 of SEQ ID NO: 26 | QRTLWGYDLYGMDY |
| 40 | 1B12.4VL | | | ETTVTQSPAFLSVTPGEKVTITCITSTDID VDMNWYQQKPDQPPKLLISQGNTLRPGVPS RFSSSGSGTDFTFTISSLEAEDAATYYCLQ SDNLPLTFGQGTKLEIK |
| 44 | 1B12.4VL | CDR L1 | Residues 24-34 of SEQ ID NO: 27 | ITSTDIDVDMN |
| 45 | 1B12.4VL | CDR L2 | Residues 50-56 of SEQ ID NO: 27 | QGNTLRP |
| 46 | 1B12.4VL | CDR L3 | Residues 89-97 of SEQ ID NO: 27 | LQSDNLPLT |
| 33 | 1B12.5VH | | | EVQLVESGGGLVQPGGSLRLSCAVSGFTLS DYGVSWIRQAPGKGLEWLGLIWGGGDTYYN SPLKSRLTISKDNSKSTVYLQMNSLRAEDT |

TABLE 8 -continued

Humanized Variable Regions Of The Murine Monoclonal Antibody 1B12

| SEQ ID No. | Protein region | | | Sequence 12345678901234567890123456789 0 |
|---|---|---|---|---|
| | | | | AVYYCAKQRTLWGYDLYGMDYWGQGTLVTVSS |
| 41 | 1B12.5VH | CDR H1 | Residues 31-35 of SEQ ID NO: 26 | DYGVS |
| 42 | 1B12.5VH | CDR H2 | Residues 50-65 of SEQ ID NO: 26 | LIWGGGDTYYNSPLKS |
| 43 | 1B12.5VH | CDR H3 | Residues 98-111 of SEQ ID NO: 26 | QRTLWGYDLYGMDY |
| 36 | 1B12.5VL | | | DTQVTQSPSSLSASVGDRVTITCITSTDID VDMNWYQQKPGKPPKLLISQGNTLRPGVPS RFSSSGSGTDFTFTISSLQPEDFATYYCLQ SDNLPLTFGQGTKLEIK |
| 44 | 1B12.5VL | CDR L1 | Residues 24-34 of SEQ ID NO: 27 | ITSTDIDVDMN |
| 45 | 1B12.5VL | CDR L2 | Residues 50-56 of SEQ ID NO: 27 | QGNTLRP |
| 46 | 1B12.5VL | CDR L3 | Residues 89-97 of SEQ ID NO: 27 | LQSDNLPLT |
| 33 | 1B12.6VH | | | EVQLVESGGGLVQPGGSLRLSCAVSGFTLS DYGVSWIRQAPGKGLEWLGLIWGGGDTYYN SPLKSRLTISKDNSKSTVYLQMNSLRAEDT AVYYCAKQRTLWGYDLYGMDYWGQGTLVTVSS |
| 41 | 1B12.6VH | CDR H1 | Residues 31-35 of SEQ ID NO: 26 | DYGVS |
| 42 | 1B12.6VH | CDR H2 | Residues 50-65 of SEQ ID NO: 26 | LIWGGGDTYYNSPLKS |
| 43 | 1B12.6VH | CDR H3 | Residues 98-111 of SEQ ID NO: 26 | QRTLWGYDLYGMDY |
| 37 | 1B12.6VL | | | ETTVTQSPSSLSASVGDRVTITCITSTDID VDMNWYQQKPGKPPKLLISQGNTLRPGVPS RFSSSGSGTDFTFTISSLQPEDFATYYCLQ SDNLPLTFGQGTKLEIK |
| 44 | 1B12.6VL | CDR L1 | Residues 24-34 of SEQ ID NO: 27 | ITSTDIDVDMN |
| 45 | 1B12.6VL | CDR L2 | Residues 50-56 of SEQ ID NO: 27 | QGNTLRP |

TABLE 8 -continued

Humanized Variable Regions Of The Murine Monoclonal Antibody 1B12

| SEQ ID No. | Protein region | | | Sequence |
|---|---|---|---|---|
| 46 | 1B12.6VL | CDR L3 | Residues 89-97 of SEQ ID NO: 27 | LQSDNLPLT |
| 33 | 1B12.7VH | | | EVQLVESGGGLVQPGGSLRLSCAVSGFTLSDYGVSWIRQAPGKGLEWLGLIWGGGDTYYNSPLKSRLTISKDNSKSTVYLQMNSLRAEDTAVYYCAKQRTLWGYDLYGMDYWGQGTLVTVSS |
| 41 | 1B12.7VH | CDR H1 | Residues 31-35 of SEQ ID NO: 26 | DYGVS |
| 42 | 1B12.7VH | CDR H2 | Residues 50-65 of SEQ ID NO: 26 | LIWGGGDTYYNSPLKS |
| 43 | 1B12.7VH | CDR H3 | Residues 98-111 of SEQ ID NO: 26 | QRTLWGYDLYGMDY |
| 39 | 1B12.7VL | | | DTVVTQSPAFLSVTPGEKVTITCITSTDIDVDMNWYQQKPDQPPKLLISQGNTLRPGVPSRFSSSGSGTDFTFTISSLEAEDAATYYCLQSDNLPLTFGQGTKLEIK |
| 44 | 1B12.7VL | CDR L1 | Residues 24-34 of SEQ ID NO: 27 | ITSTDIDVDMN |
| 45 | 1B12.7VL | CDR L2 | Residues 50-56 of SEQ ID NO: 27 | QGNTLRP |
| 46 | 1B12.7VL | CDR L3 | Residues 89-97 of SEQ ID NO: 27 | LQSDNLPLT |
| 33 | 1B12.8VH | | | EVQLVESGGGLVQPGGSLRLSCAVSGFTLSDYGVSWIRQAPGKGLEWLGLIWGGGDTYYNSPLKSRLTISKDNSKSTVYLQMNSLRAEDTAVYYCAKQRTLWGYDLYGMDYWGQGTLVTVSS |
| 41 | 1B12.8VH | CDR H1 | Residues 31-35 of SEQ ID NO: 26 | DYGVS |
| 42 | 1B12.8VH | CDR H2 | Residues 50-65 of SEQ ID NO: 26 | LIWGGGDTYYNSPLKS |
| 43 | 1B12.8VH | CDR H3 | Residues 98-111 of SEQ ID NO: 26 | QRTLWGYDLYGMDY |
| 40 | 1B12.8VL | | | ETTVTQSPAFLSVTPGEKVTITCITSTDIDVDMNWYQQKPDQPPKLLISQGNTLRPGVPSRFSSSGSGTDFTFTISSLEAEDAATYYCLQSDNLPLTFGQGTKLEIK |

TABLE 8 -continued

Humanized Variable Regions Of The Murine Monoclonal Antibody 1B12

| SEQ ID No. | Protein region | | | Sequence 12345678901234567890123456789 |
|---|---|---|---|---|
| 44 | 1B12.8VL | CDR L1 | Residues 24-34 of SEQ ID NO: 27 | ITSTDIDVDMN |
| 45 | 1B12.8VL | CDR L2 | Residues 50-56 of SEQ ID NO: 27 | QGNTLRP |
| 46 | 1B12.8VL | CDR L3 | Residues 89-97 of SEQ ID NO: 27 | LQSDNLPLT |

Example 3

Functional Characterization Of Human IL-1β Antibodies

Example 3.1

IL-1β Enzyme-Linked Immunosorbent Assay Protocol

To determine if anti-IL-1β mAbs bind to human IL-1β, ELISA plates (Nunc, MaxiSorp, Rochester, N.Y.) were incubated overnight at 4° C. with anti-human Fc antibody diluted in Pierce Coat buffer at 2 µg/ml (Jackson Immunoresearch, West Grove, Pa.). Plates were washed five times in washing buffer (PBS containing 0.05% Tween 20), and blocked for 1 hour at 25° C. with 200 µl per well superblock blocking buffer (Thermo scientific, #37515). Blocking buffer was removed by tapping plates, and 2 µg/ml of each antibody in PBS containing 10% superblock, 0.5% tween-20 was added to the wells at 100 µl per well and incubated at 25° C. for 1 hour. The wells were washed five times in 1×PBST, and 1 µg/ml biotinylated antigen was titrated at 1:6 serial dilutions (for a range of µg to pg in PBS containing 10% superblock, 0.05% tween 20). Each dilution of antigen was then added to the plates and incubated for 1 hour at 25° C. The wells were washed five times in 1×PBST and incubated for 1 hour at 25° C. with polyHRP streptavidin (KPL #474-3000, Gaithersburg, Md.). The wells were washed five times in 1×PBST, and 100 µl of ULTRA-TMB ELISA (Pierce, Rockford, Ill.) were added per well. Following color development the reaction was stopped with 1N HCL and absorbance at 450 nM was measured. The results are shown in Table 9, and the numerical value indicating binding of human anti-IL-1β antibodies to human IL-1β.

TABLE 9

Binding Of Humanized Antibodies To Human IL-1β by ELISA

| Anti-IL-1β mAb | EC50 in hIL-1β ELISA (pM) |
|---|---|
| 1B12.1 | 39.9 |
| 1B12.2 | 37.6 |
| 1B12.3 | 43.8 |
| 1B12.4 | 37.8 |
| 1B12.5 | 48.8 |
| 1B12.6 | 45.9 |
| 1B12.7 | 58.2 |
| 1B12.8 | 47.9 |

Example 3.2

Neutralizing Potency Of Humanized IL-1β Antibodies

To examine the functional activity of the anti-human IL-1β antibodies in the invention, the antibodies were used in the MRC-5 assay that measures the ability of the antibody to inhibit IL-1β activity. The MRC-5 cell line is a human lung fibroblast cell line that produces IL-8 in response to human IL-1β in a dose-dependent manner. MRC-5 cells were originally obtained from ATCC and subcultured in 10% FBS complete MEM and grown at 37° C. in a 5% $CO_2$ incubator. To determine an antibody's neutralizing potency against IL-1β, antibodies (50 ul) were added to a 96 well plate ($1 \times 10^{-7}$ to $1 \times 10^{-15}$ M final concentration range) and pre-incubated with 50 ul of human IL-1β (50 pg/mL final concentration) for 1 hr at 37° C., 5% $CO_2$. Antigen antibody complexes (100 uL) were then added to MRC-5 cells (plated 24 hours previously at a concentration of 1 E5/ml at 100 ul cells/well). Assay plates were incubated overnight at 37° C. in a 5% $CO_2$ incubator. Antibody potency was determined by its ability to inhibit IL-8 production. Human IL-8 production was measured by a chemiluminescence-based assay. Table 10 summarizes antibody potencies to human IL-1β.

TABLE 10

Neutralizing Potency Of Humanized IL-1β Antibodies

| Anti-IL-1β mAb | Potency on Human IL-1β $IC_{50}$ (pM) |
|---|---|
| 1B12.1 | 151 |
| 1B12.2 | 146 |
| 1B12.3 | 303 |
| 1B12.4 | 597 |
| 1B12.5 | 319 |
| 1B12.6 | 378 |
| 1B12.7 | 581 |
| 1B12.8 | 484 |

Example 3.3

Affinity Measurement Of IL-1β Antibodies By Surface Plasmon Resonance

The BIACORE® assay (Biacore, Inc., Piscataway, N.J.) determines the affinity of antibodies with kinetic measurements of on-, off-rate constants. Binding of antibodies to recombinant purified human IL-1β was determined by surface plasmon resonance-based measurements with a Biacore™ 3000 instrument (Biacore™ AB, Uppsala, Sweden) using running HBS-EP (10 mM HEPES [pH 7.4], 150 mM NaCl, 3 mM EDTA, and 0.005% surfactant P20) at 25° C. All chemicals were obtained from Biacore® AB (Uppsala, Sweden) unless otherwise stated. Approximately 5,000 RU of goat anti-mouse IgG, (Fcγ), fragment specific polyclonal antibody (Pierce Biotechnology Inc, Rockford, Ill.) diluted in 10 mM sodium acetate (pH 4.5) was directly immobilized across a CM5 research grade biosensor chip using a standard amine coupling kit according to manufacturer's instructions and procedures at 25 µg/ml. Unreacted moieties on the biosensor surface were blocked with ethanolamine. Modified carboxymethyl dextran surface in flowcell 2 and 4 was used as a reaction surface. Unmodified carboxymethyl dextran without goat anti-mouse IgG in flow cell 1 and 3 was used as the reference surface. For kinetic analysis, rate equations derived from the 1:1 Langmuir binding model were fitted simultaneously to association and dissociation phases of all eight injections (using global fit analysis) with the use of Biaevaluation 4.0.1 software. Purified antibodies were diluted in HEPES-buffered saline for capture across goat anti-mouse IgG specific reaction surfaces. Mouse antibodies to be captured as a ligand (25 µg/ml) were injected over reaction matrices at a flow rate of 5 µl/minute. The association and dissociation rate constants, $k_{on}$ (unit $M^{-1}s^{-1}$) and $k_{off}$ (unit $s^{-1}$) were determined under a continuous flow rate of 25 µl/minute. Rate constants were derived by making kinetic binding measurements at ten different antigen concentrations ranging from 10-200 nM. The equilibrium dissociation constant (unit M) of the reaction between antibodies and the target antigen was then calculated from the kinetic rate constants by the following formula: $K_D = k_{off}/k_{on}$. Binding is recorded as a function of time and kinetic rate constants are calculated. In this assay, on-rates as fast as $10^6 M^{-1}s^{-1}$ and off-rates as slow as $10^{-6} s^{-1}$ can be measured. Table 11 shows the affinity measurements for human anti-IL-1β antibodies.

TABLE 11

Affinity of Humanized Antibodies To Human IL-1β By Biacore

| | $K_a$ (1/Ms) | $K_d$ (1/s) | $K_D$ (M) |
|---|---|---|---|
| 1B12.1 | 5.55E+06 | 1.03E−03 | 1.86E−10 |
| 1B12.2 | 6.13E+06 | 0.90E−03 | 1.47E−10 |
| 1B12.3 | 5.73E+06 | 1.18E−03 | 2.06E−10 |
| 1B12.4 | 6.01E+06 | 0.97E−03 | 1.61E−10 |
| 1B12.5 | 6.24E+06 | 1.44E−03 | 2.31E−10 |
| 1B12.6 | 6.20E+06 | 1.25E−03 | 2.02E−10 |
| 1B12.7 | 5.76E+06 | 1.64E−03 | 2.84E−10 |
| 1B12.8 | 5.94E+06 | 1.37E−03 | 2.30E−10 |

The present invention incorporates by reference in their entirety techniques well known in the field of molecular biology. These techniques include, but are not limited to, techniques described in the following publications:

Ausubel et al. eds., Short Protocols In Molecular Biology (4th Ed. 1999) John Wiley & Sons, NY (ISBN 0-471-32938-X).

Lu and Weiner eds., Cloning and Expression Vectors for Gene Function Analysis (2001) BioTechniques Press, Westborough, Mass., 298 pp. (ISBN 1-881299-21-X).

Kontermann and Dübel eds., Antibody Engineering (2001) Springer-Verlag, NY, 790 pp. (ISBN 3-540-41354-5).

Old and Primrose, Principles of Gene Manipulation: An Introduction To Genetic Engineering (3d Ed. 1985) Blackwell Scientific Publications, Boston, Mass. Studies in Microbiology; V. 2:409 pp. (ISBN 0-632-01318-4).

Sambrook et al., Molecular Cloning: A Laboratory Manual, 2d ed. (Cold Spring Harbor Laboratory Press, Cold Spring Harbor, N.Y.), Vols. 1-3 (ISBN 0-87969-309-6).

Winnacker, From Genes To Clones: Introduction To Gene Technology (1987) VCH Publishers, NY (translated by Horst Ibelgaufts), 634 pp. (ISBN 0-89573-614-4).

Incorporation by Reference

The contents of all cited references (including literature references, patents, patent applications, and websites) that maybe cited throughout this application are hereby expressly incorporated by reference in their entirety for any purpose, as are the references cited therein. The practice of the present invention will employ, unless otherwise indicated, conventional techniques of immunology, molecular biology and cell biology, which are well known in the art.

Equivalents

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

We claim:

1. A binding protein capable of binding IL-1β wherein said binding protein comprises residues 31-35 of SEQ ID NO:26 (CDR-H1); residues 50-65 of SEQ ID NO:26 (CDR-H2); residues 98-111 of SEQ ID NO:26 (CDR-H3); residues 24-34 of SEQ ID NO:27 (CDR-L1); residues 50-56 of SEQ ID NO:27 (CDR-L2); and residues 89-97 of SEQ ID NO:27 (CDR-L3), said binding protein comprising a variable heavy chain polypeptide comprising an amino acid sequence selected from the group consisting of SEQ ID NO: 28, SEQ ID NO: 29, SEQ ID NO: 30, SEQ ID NO: 31, SEQ ID NO: 32, and SEQ ID NO: 33, and a variable light chain polypeptide comprising an amino acid sequence selected from the group consisting of SEQ ID NO: 34, SEQ ID NO: 35, SEQ ID NO: 36, SEQ ID NO: 37, SEQ ID NO: 38, SEQ ID NO: 39 and SEQ ID NO: 40.

2. The binding protein of claim 1, wherein said binding protein comprises a variable heavy chain polypeptide and a variable light chain polypeptide comprising the amino acid sequences: SEQ ID NO: 30 and SEQ ID NO: 36, respectively; SEQ ID NO: 30 and SEQ ID NO: 37, respectively; SEQ ID NO: 30 and SEQ ID NO: 39, respectively; SEQ ID NO: 30 and SEQ ID NO: 40, respectively; SEQ ID NO: 33 and SEQ ID NO: 36, respectively; and SEQ ID NO: 33 and SEQ ID NO: 37, respectively; and SEQ ID NO: 33 and SEQ ID NO: 39, respectively; SEQ ID NO: 33 and SEQ ID NO: 40, respectively.

3. The binding protein of claim 1, wherein said binding protein is selected from the group consisting of: an immunoglobulin molecule, a disulfide linked Fv, a monoclonal antibody, an scFv, a chimeric antibody, a single domain antibody, a CDR-grafted antibody, a diabody, a humanized antibody, a multispecific antibody, an Fab, a dual specific antibody, a DVD-Ig protein, a Fab', a bispecific antibody, a F(ab')2, and a Fv.

4. The binding protein of claim 1, wherein said binding protein comprises a heavy chain immunoglobulin constant domain selected from the group consisting of a human IgM constant domain, a human IgG4 constant domain, a human IgG1 constant domain, a human IgE constant domain, a human IgG2 constant domain, a human IgG3 constant domain, and a human IgA constant domain.

5. The binding protein of claim 1, further comprising a heavy chain constant region comprising an amino acid sequence selected from the group consisting of SEQ ID NO: 2 and SEQ ID NO: 3.

6. The binding protein of claim 1, further comprising a light chain constant region comprising an amino acid sequence selected from the group consisting of SEQ ID NO: 4 and SEQ ID NO: 5.

7. The binding protein of claim 1, wherein said binding protein is capable of neutralizing human IL-1β.

8. The binding protein of claim 1, wherein said binding protein has an on rate constant (Kon) to said target selected from the group consisting of at least about $10^2 M^{-1}s^{-1}$; at least about $10^3 M^{-1}s^{-1}$; at least about $10^4 M^{-1}s^{-1}$; at least about $10^5 M^{-1}s^{-1}$; and at least about $10^6 M^{-1}s^{-1}$ as measured by surface plasmon resonance.

9. The binding protein of claim 1, wherein said binding protein has an off rate constant (Koff) to said target selected from the group consisting of at most about $10^{-3}s^{-1}$; at most about $10^{-4}s^{-1}$; at most about $10^{-5}s^{-1}$; and at most about $10^{-6}s^{-1}$, as measured by surface plasmon resonance.

10. The binding protein of claim 1, wherein said binding protein has a dissociation constant (KD) to said target selected from the group consisting of at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M.

11. The binding protein of claim 10, where said binding protein has a dissociation constant (KD) to IL-1a selected from the group consisting of about $1.31 \times 10^{-10}$M; about $1.47 \times 10^{-10}$M; about $1.61 \times 10^{-10}$M; about $1.86 \times 10^{-10}$M; about $2.02 \times 10^{-10}$M; about $2.06 \times 10^{-10}$M; about $2.3 \times 10^{-10}$M; and about $2.84 \times 10^{-10}$M.

12. The binding protein of claim 1, wherein said binding protein further comprises an agent selected from the group consisting of an immunoadhesion molecule, an imaging agent, a therapeutic agent, and a cytotoxic agent.

13. The binding protein of claim 12, wherein said agent is an imaging agent selected from the group consisting of a radiolabel, an enzyme, a fluorescent label, a luminescent label, a bioluminescent label, a magnetic label, and biotin.

14. The binding protein of claim 12, wherein said imaging agent is a radiolabel selected from the group consisting of: 3H, 14C, 35S, 90Y, 99Tc, 111In, 125I, 131I, 177Lu, 166Ho, and 153Sm.

15. The binding protein of claim 12, wherein said agent is a therapeutic or cytotoxic agent selected from the group consisting of an anti-metabolite, an alkylating agent, an antibiotic, a growth factor, a cytokine, an anti-angiogenic agent, an anti-mitotic agent, an anthracycline, toxin, and an apoptotic agent.

16. The binding protein of claim 1, wherein said binding protein is a crystallized binding protein.

17. The binding protein of claim 16, wherein said crystallized binding protein is a carrier-free pharmaceutical controlled release crystallized binding protein.

18. The binding protein of claim 17, wherein said crystallized binding protein has a greater half life in vivo than its non-crystallized counterpart.

19. The binding protein of claim 17, wherein said crystallized binding protein retains the IL-1β binding activity of its non-crystallized counterpart.

20. A composition for the release of a binding protein, said composition comprising:

(a) a formulation, wherein said formulation comprises the crystallized binding protein of claim 16, and an ingredient; and
(b) at least one polymeric carrier.

21. The composition of claim 20, wherein said polymeric carrier is a polymer selected from the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone); poly (ethylene glycol), poly ((hydroxypropyl) methacrylamide, poly [(organo) phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, and sulfated polysaccharides, and blends and copolymers thereof.

22. The composition of claim 20, wherein said ingredient is selected from the group consisting of albumin, sucrose, trehalose, lactitol, gelatin, hydroxypropyl-b-cyclodextrin, methoxypolyethylene glycol and polyethylene glycol.

23. A pharmaceutical composition comprising the binding protein of claim 1, and a pharmaceutically acceptable carrier.

24. The pharmaceutical composition of claim 23, wherein said pharmaceutically acceptable carrier functions as adjuvant to increase the absorption, or dispersion of said binding protein.

25. The pharmaceutical composition of claim 24, wherein said adjuvant is hyaluronidase.

26. The pharmaceutical composition of claim 23, further comprising at least one additional agent.

27. The pharmaceutical composition of claim 26, wherein said additional agent is selected from the group consisting of: a therapeutic agent; an imaging agent; a cytotoxic agent; an angiogenesis inhibitor; a kinase inhibitor; a co-stimulation molecule blocker; an adhesion molecule blocker; an anti-cytokine antibody or functional fragment thereof; methotrexate; cyclosporin; rapamycin; FK506; a detectable label or reporter; a TNF antagonist; an anti-rheumatic; a muscle relaxant; a narcotic; a non-steroid anti-inflammatory drug (NSAID); an analgesic; an anesthetic; a sedative; a local anesthetic; a neuromuscular blocker; an antimicrobial; an antipsoriatic; a corticosteroid; an anabolic steroid; an erythropoietin; an immunization; an immunoglobulin; an immunosuppressive; a growth hormone; a hormone replacement drug; a radiopharmaceutical; an antidepressant; an antipsychotic; a stimulant; an asthma medication; a beta agonist; an inhaled steroid; an oral steroid; an epinephrine or analog thereof; a cytokine; and a cytokine antagonist.

* * * * *

SEQUENCE LISTING

<160> NUMBER OF SEQ ID NOS: 46

<210> SEQ ID NO 1
<211> LENGTH: 153
<212> TYPE: PRT
<213> ORGANISM: Homo sapiens

```
<400> SEQUENCE: 1

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140

Asp Phe Thr Met Gln Phe Val Ser Ser
145                 150

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Phe Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 4
<211> LENGTH: 106
<212> TYPE: PRT
<213> ORGANISM: Homo sapiens

<400> SEQUENCE: 4

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105

<210> SEQ ID NO 5
<211> LENGTH: 105
<212> TYPE: PRT
<213> ORGANISM: Homo sapiens

<400> SEQUENCE: 5

Gln Pro Lys Ala Ala Pro Ser Val Thr Leu Phe Pro Pro Ser Ser Glu
1               5                   10                  15
Glu Leu Gln Ala Asn Lys Ala Thr Leu Val Cys Leu Ile Ser Asp Phe
            20                  25                  30
Tyr Pro Gly Ala Val Thr Val Ala Trp Lys Ala Asp Ser Ser Pro Val
        35                  40                  45
Lys Ala Gly Val Glu Thr Thr Thr Pro Ser Lys Gln Ser Asn Asn Lys
    50                  55                  60
Tyr Ala Ala Ser Ser Tyr Leu Ser Leu Thr Pro Glu Gln Trp Lys Ser
65                  70                  75                  80
His Arg Ser Tyr Ser Cys Gln Val Thr His Glu Gly Ser Thr Val Glu
                85                  90                  95
Lys Thr Val Ala Pro Thr Glu Cys Ser
            100                 105

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (3)..(3)
<223> OTHER INFORMATION: Any amino acid

<400> SEQUENCE: 6

Phe Gly Xaa Gly
1

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(9)
<223> OTHER INFORMATION: Any amino acid

<400> SEQUENCE: 7

Cys Xaa Xaa Xaa Xaa Xaa Xaa Xaa Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Glu Trp Ile Gly
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 9

Trp Gly Xaa Gly
1

<210> SEQ ID NO 10
<211> LENGTH: 30
<212> TYPE: PRT
<213> ORGANISM: Homo sapiens

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 11
<211> LENGTH: 14
<212> TYPE: PRT
<213> ORGANISM: Homo sapiens
```

<400> SEQUENCE: 11

Trp Ile Arg Gln Pro Pro Gly Lys Gly Leu Glu Trp Ile Gly
1               5                   10

<210> SEQ ID NO 12
<211> LENGTH: 32
<212> TYPE: PRT
<213> ORGANISM: Homo sapiens

<400> SEQUENCE: 12

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 13
<211> LENGTH: 11
<212> TYPE: PRT
<213> ORGANISM: Homo sapiens

<400> SEQUENCE: 13

Trp Gly Gln Gly Thr Leu Val Thr Val Ser Ser
1               5                   10

<210> SEQ ID NO 14
<211> LENGTH: 30
<212> TYPE: PRT
<213> ORGANISM: Homo sapiens

<400> SEQUENCE: 14

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser
            20                  25                  30

<210> SEQ ID NO 15
<211> LENGTH: 14
<212> TYPE: PRT
<213> ORGANISM: Homo sapiens

<400> SEQUENCE: 15

Trp Val Arg Gln Ala Pro Gly Lys Gly Leu Glu Trp Val Ser
1               5                   10

<210> SEQ ID NO 16
<211> LENGTH: 32
<212> TYPE: PRT
<213> ORGANISM: Homo sapiens

<400> SEQUENCE: 16

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 17
<211> LENGTH: 11
<212> TYPE: PRT
<213> ORGANISM: Homo sapiens

<400> SEQUENCE: 17

Trp Gly Gln Gly Thr Leu Val Thr Val Ser Ser
1               5                   10

```
<210> SEQ ID NO 18
<211> LENGTH: 23
<212> TYPE: PRT
<213> ORGANISM: Homo sapiens

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 19
<211> LENGTH: 15
<212> TYPE: PRT
<213> ORGANISM: Homo sapiens

<400> SEQUENCE: 19

Trp Tyr Gln Gln Lys Pro Gly Lys Ala Pro Lys Leu Leu Ile Tyr
1               5                   10                  15

<210> SEQ ID NO 20
<211> LENGTH: 32
<212> TYPE: PRT
<213> ORGANISM: Homo sapiens

<400> SEQUENCE: 20

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 21
<211> LENGTH: 10
<212> TYPE: PRT
<213> ORGANISM: Homo sapiens

<400> SEQUENCE: 21

Phe Gly Gln Gly Thr Lys Leu Glu Ile Lys
1               5                   10

<210> SEQ ID NO 22
<211> LENGTH: 23
<212> TYPE: PRT
<213> ORGANISM: Homo sapiens

<400> SEQUENCE: 22

Asp Val Val Met Thr Gln Ser Pro Ala Phe Leu Ser Val Thr Pro Gly
1               5                   10                  15

Glu Lys Val Thr Ile Thr Cys
            20

<210> SEQ ID NO 23
<211> LENGTH: 15
<212> TYPE: PRT
<213> ORGANISM: Homo sapiens

<400> SEQUENCE: 23

Trp Tyr Gln Gln Lys Pro Asp Gln Ala Pro Lys Leu Leu Ile Lys
1               5                   10                  15

<210> SEQ ID NO 24
<211> LENGTH: 32
<212> TYPE: PRT
```

<213> ORGANISM: Homo sapiens

<400> SEQUENCE: 24

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30

<210> SEQ ID NO 25
<211> LENGTH: 10
<212> TYPE: PRT
<213> ORGANISM: Homo sapiens

<400> SEQUENCE: 25

Phe Gly Gln Gly Thr Lys Leu Glu Ile Lys
1               5                   10

<210> SEQ ID NO 26
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val His Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Asp Thr Tyr Tyr Asn Ser Pro Leu Lys
    50                  55                  60

Ser Arg Leu Ser Ile Arg Lys Asp Asn Ser Lys Ser Gln Val Phe Leu
65                  70                  75                  80

Lys Met Asn Ser Leu Gln Thr Asp Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Ser Val Thr Val Ser Ser
        115                 120

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Val Asp
            20                  25                  30

Met Asn Trp Tyr Gln Gln Lys Pro Gly Glu Pro Pro Lys Leu Leu Ile
        35                  40                  45

Ser Gln Gly Asn Thr Leu Arg Pro Gly Val Pro Ser Arg Phe Ser Ser
    50                  55                  60

Ser Gly Ser Gly Thr Asp Phe Val Phe Ile Ile Glu Asn Met Leu Ser

```
                65                  70                  75                  80
Glu Asp Val Ala Asp Tyr Tyr Cys Leu Gln Ser Asp Asn Leu Pro Leu
                    85                  90                  95

Thr Phe Gly Ala Gly Thr Lys Leu Glu Leu Lys
                100                 105
```

<210> SEQ ID NO 28
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asp Tyr
                20                  25                  30

Gly Val Ser Trp Ile Arg Gln Pro Pro Gly Lys Gly Leu Glu Trp Ile
            35                  40                  45

Gly Leu Ile Trp Gly Gly Gly Asp Thr Tyr Tyr Asn Ser Pro Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gln Arg Thr Leu Trp Gly Tyr Asp Leu Tyr Gly Met Asp Tyr Trp
                100                 105                 110

Gly Gln Gly Thr Leu Val Thr Val Ser Ser
            115                 120
```

<210> SEQ ID NO 29
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asp Tyr
                20                  25                  30

Gly Val Ser Trp Ile Arg Gln Pro Pro Gly Lys Gly Leu Glu Trp Ile
            35                  40                  45

Gly Leu Ile Trp Gly Gly Gly Asp Thr Tyr Tyr Asn Ser Pro Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gln Arg Thr Leu Trp Gly Tyr Asp Leu Tyr Gly Met Asp Tyr Trp
                100                 105                 110

Gly Gln Gly Thr Leu Val Thr Val Ser Ser
            115                 120
```

<210> SEQ ID NO 30

```
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 31
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Asp Tyr
            20                  25                  30

Gly Val Ser Trp Val Arg Gln Ala Pro Gly Lys Gly Leu Glu Trp Val
        35                  40                  45

Ser Leu Ile Trp Gly Gly Gly Asp Thr Tyr Tyr Asn Ser Pro Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 32
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Glu Ser Gly Gly Gly Leu Val Gln Pro Gly Gly
```

```
                    1               5                   10                  15

Ser Leu Arg Leu Ser Cys Ala Ala Ser Gly Phe Thr Phe Ser Asp Tyr
            20                  25                  30

Gly Val Ser Trp Val Arg Gln Ala Pro Gly Lys Gly Leu Glu Trp Val
            35                  40                  45

Ser Leu Ile Trp Gly Gly Asp Thr Tyr Tyr Asn Ser Pro Leu Lys
50                      55                  60

Ser Arg Phe Thr Ile Ser Arg Asp Asn Ser Lys Asn Thr Leu Tyr Leu
65                      70                  75                  80

Gln Met Asn Ser Leu Arg Ala Glu Asp Thr Ala Val Tyr Tyr Cys Ala
            85                  90                  95

Arg Gln Arg Thr Leu Trp Gly Tyr Asp Leu Tyr Gly Met Asp Tyr Trp
            100                 105                 110

Gly Gln Gly Thr Leu Val Thr Val Ser Ser
            115                 120

<210> SEQ ID NO 33
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Leu Ser Asp Tyr
            20                  25                  30

Gly Val Ser Trp Ile Arg Gln Ala Pro Gly Lys Gly Leu Glu Trp Leu
            35                  40                  45

Gly Leu Ile Trp Gly Gly Asp Thr Tyr Tyr Asn Ser Pro Leu Lys
50                      55                  60

Ser Arg Leu Thr Ile Ser Lys Asp Asn Ser Lys Ser Thr Val Tyr Leu
65                      70                  75                  80

Gln Met Asn Ser Leu Arg Ala Glu Asp Thr Ala Val Tyr Tyr Cys Ala
            85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
            115                 120

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Ile Thr Ser Thr Asp Ile Asp Val Asp
            20                  25                  30

Met Asn Trp Tyr Gln Gln Lys Pro Gly Lys Ala Pro Lys Leu Leu Ile
            35                  40                  45

Tyr Gln Gly Asn Thr Leu Arg Pro Gly Val Pro Ser Arg Phe Ser Gly
50                      55                  60
```

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Asn Leu Pro Leu
                85                  90                  95

Thr Phe Gly Gln Gly Thr Lys Leu Glu Ile Lys
            100                 105

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Ile Thr Ser Thr Asp Ile Asp Val Asp
                20                  25                  30

Met Asn Trp Tyr Gln Gln Lys Pro Gly Lys Ala Pro Lys Leu Leu Ile
            35                  40                  45

Tyr Gln Gly Asn Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Ser Asp Asn Leu Pro Leu
                85                  90                  95

Thr Phe Gly Gln Gly Thr Lys Leu Glu Ile Lys
            100                 105

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Thr Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Val Asp
                20                  25                  30

Met Asn Trp Tyr Gln Gln Lys Pro Gly Lys Pro Pro Lys Leu Leu Ile
            35                  40                  45

Ser Gln Gly Asn Thr Leu Arg Pro Gly Val Pro Ser Arg Phe Ser Ser
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Asn Leu Pro Leu
                85                  90                  95

Thr Phe Gly Gln Gly Thr Lys Leu Glu Ile Lys
            100                 105

<210> SEQ ID NO 37
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 37

Glu Thr Thr Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Val Asp
            20                  25                  30

Met Asn Trp Tyr Gln Gln Lys Pro Gly Lys Pro Lys Leu Leu Ile
        35                  40                  45

Ser Gln Gly Asn Thr Leu Arg Pro Gly Val Pro Ser Arg Phe Ser Ser
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Asn Leu Pro Leu
                85                  90                  95

Thr Phe Gly Gln Gly Thr Lys Leu Glu Ile Lys
            100                 105

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Val Val Met Thr Gln Ser Pro Ala Phe Leu Ser Val Thr Pro Gly
1               5                   10                  15

Glu Lys Val Thr Ile Thr Cys Ile Thr Ser Thr Asp Ile Asp Val Asp
            20                  25                  30

Met Asn Trp Tyr Gln Gln Lys Pro Asp Gln Ala Pro Lys Leu Leu Ile
        35                  40                  45

Lys Gln Gly Asn Thr Leu Arg Pro Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Leu Gln Ser Asp Asn Leu Pro Leu
                85                  90                  95

Thr Phe Gly Gln Gly Thr Lys Leu Glu Ile Lys
            100                 105

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Thr Val Val Thr Gln Ser Pro Ala Phe Leu Ser Val Thr Pro Gly
1               5                   10                  15

Glu Lys Val Thr Ile Thr Cys Ile Thr Ser Thr Asp Ile Asp Val Asp
            20                  25                  30

Met Asn Trp Tyr Gln Gln Lys Pro Asp Gln Pro Pro Lys Leu Leu Ile
        35                  40                  45

Ser Gln Gly Asn Thr Leu Arg Pro Gly Val Pro Ser Arg Phe Ser Ser
    50                  55                  60

```
Ser Gly Ser Gly Thr Asp Phe Thr Phe Thr Ile Ser Ser Leu Glu Ala
 65                  70                  75                  80

Glu Asp Ala Ala Thr Tyr Tyr Cys Leu Gln Ser Asp Asn Leu Pro Leu
                 85                  90                  95

Thr Phe Gly Gln Gly Thr Lys Leu Glu Ile Lys
            100                 105
```

<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Glu Thr Thr Val Thr Gln Ser Pro Ala Phe Leu Ser Val Thr Pro Gly
 1               5                  10                  15

Glu Lys Val Thr Ile Thr Cys Ile Thr Ser Thr Asp Ile Asp Val Asp
                 20                  25                  30

Met Asn Trp Tyr Gln Gln Lys Pro Asp Gln Pro Pro Lys Leu Leu Ile
             35                  40                  45

Ser Gln Gly Asn Thr Leu Arg Pro Gly Val Pro Ser Arg Phe Ser Ser
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Leu Gln Ser Asp Asn Leu Pro Leu
                 85                  90                  95

Thr Phe Gly Gln Gly Thr Lys Leu Glu Ile Lys
            100                 105
```

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Asp Tyr Gly Val Ser
 1               5
```

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Leu Ile Trp Gly Gly Gly Asp Thr Tyr Tyr Asn Ser Pro Leu Lys Ser
 1               5                  10                  15
```

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Gln Arg Thr Leu Trp Gly Tyr Asp Leu Tyr Gly Met Asp Tyr
1               5                  10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Thr Ser Thr Asp Ile Asp Val Asp Met Asn
1               5                  10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Gly Asn Thr Leu Arg Pro
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Gln Ser Asp Asn Leu Pro Leu Thr
1               5
```